US009170154B2

(12) United States Patent
Myrick et al.

(10) Patent No.: US 9,170,154 B2
(45) Date of Patent: Oct. 27, 2015

(54) DATA VALIDATION AND CLASSIFICATION IN OPTICAL ANALYSIS SYSTEMS

(75) Inventors: Michael L. Myrick, Irmo, SC (US);
Ryan J. Priore, Columbia, SC (US);
Robert P. Freese, Pittsboro, NC (US);
John C. Blackburn, Charleston, SC (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 1777 days.

(21) Appl. No.: 12/295,631

(22) PCT Filed: Jun. 26, 2007

(86) PCT No.: PCT/US2007/072095
§ 371 (c)(1),
(2), (4) Date: Apr. 20, 2009

(87) PCT Pub. No.: WO2008/002903
PCT Pub. Date: Jan. 3, 2008

(65) Prior Publication Data
US 2009/0299946 A1     Dec. 3, 2009

Related U.S. Application Data

(60) Provisional application No. 60/816,461, filed on Jun. 26, 2006.

(51) Int. Cl.
*G06N 5/00* (2006.01)
*G06F 1/00* (2006.01)
(Continued)

(52) U.S. Cl.
CPC .... *G01J 3/28* (2013.01); *G01J 3/02* (2013.01);
*G01J 3/0291* (2013.01); *G01J 3/10* (2013.01);
*G01J 2003/1213* (2013.01); *G01J 2003/2866* (2013.01); *G01N 2201/129* (2013.01)

(58) Field of Classification Search
USPC .......................................................... 706/52
See application file for complete search history.

(56) References Cited

U.S. PATENT DOCUMENTS

| 3,632,435 A | 1/1972 | Eriksson et al. |
| 3,717,078 A | 2/1973 | Ogura |

(Continued)

FOREIGN PATENT DOCUMENTS

| EP | 0 600 334 A2 | 6/1996 |
| EP | 1969326 A1 | 9/2008 |

(Continued)

OTHER PUBLICATIONS

M.L. Myrick et al., "Application of Multivariate Optical Computing to Near-Infrared Imaging", Vibration Spectroscopy-based Sensor System, Proceedings of SPIE, vol. 4577, pp. 148-157, 2002.

(Continued)

*Primary Examiner* — Jeffrey A Gaffin
*Assistant Examiner* — Kalpana Bharadwaj

(57) ABSTRACT

A method of classifying information in an optical analysis system includes obtaining calibration data defining a plurality of data points, each data point representing values for two or more detectors when sampling a material used to construct a multivariate optical element. Based on the calibration data, one or more validation models can be developed to indicate one or more ranges of expected results. Validation data comprising the models can be used to compare data points representing values for two or more detectors when performing a measurement of a material to determine if the data points fall within an expected range. Classification data can be generated based on the comparison and, in some embodiments, one or more indicators, such as a confidence level in a measurement, can be provided.

29 Claims, 6 Drawing Sheets

(51) Int. Cl.
  *G01J 3/28* (2006.01)
  *G01J 3/02* (2006.01)
  *G01J 3/10* (2006.01)
  *G01J 3/12* (2006.01)

(56) References Cited

U.S. PATENT DOCUMENTS

| | | |
|---|---|---|
| 3,761,724 A | 9/1973 | Dennis |
| 4,084,880 A | 4/1978 | Clow |
| 4,118,106 A | 10/1978 | Leith |
| 4,499,378 A | 2/1985 | Miyatake et al. |
| 4,595,832 A | 6/1986 | LaDelfe et al. |
| 4,607,914 A | 8/1986 | Fienup |
| 4,687,335 A | 8/1987 | Zupanick et al. |
| 4,687,337 A | 8/1987 | Stewart et al. |
| 4,704,536 A | 11/1987 | Sugiyama et al. |
| 4,821,338 A | 4/1989 | Naruse et al. |
| 4,891,574 A | 1/1990 | Nagaya et al. |
| 4,917,958 A | 4/1990 | Akai et al. |
| 4,934,782 A | 6/1990 | Soffer et al. |
| 4,968,148 A | 11/1990 | Chow et al. |
| 4,981,332 A | 1/1991 | Smith |
| 5,005,946 A | 4/1991 | Brandstetter |
| 5,029,245 A | 7/1991 | Keranen et al. |
| 5,071,526 A | 12/1991 | Pletcher et al. |
| 5,090,807 A | 2/1992 | Tai |
| 5,103,340 A | 4/1992 | Dono et al. |
| 5,137,364 A | 8/1992 | McCarthy |
| 5,150,236 A | 9/1992 | Patel |
| 5,194,921 A | 3/1993 | Tambo et al. |
| 5,223,715 A | 6/1993 | Taylor |
| 5,259,381 A | 11/1993 | Cheung et al. |
| 5,289,289 A | 2/1994 | Nagasaki |
| 5,321,539 A | 6/1994 | Hirbayashi et al. |
| 5,406,082 A | 4/1995 | Pearson et al. |
| 5,412,465 A | 5/1995 | Baylor et al. |
| 5,424,545 A | 6/1995 | Block et al. |
| 5,459,677 A | 10/1995 | Kowalski et al. |
| 5,479,164 A | 12/1995 | Yorks et al. |
| 5,504,332 A | 4/1996 | Richmond et al. |
| 5,513,022 A | 4/1996 | Son et al. |
| 5,555,128 A | 9/1996 | Khoury et al. |
| 5,622,868 A | 4/1997 | Clarke et al. |
| 5,641,962 A | 6/1997 | Perry et al. |
| 5,710,655 A | 1/1998 | Rumbaugh et al. |
| 5,717,605 A | 2/1998 | Komiya et al. |
| 5,734,098 A | 3/1998 | Kraus et al. |
| 5,737,076 A | 4/1998 | Glaus et al. |
| 5,747,806 A | 5/1998 | Khalil et al. |
| 5,750,994 A | 5/1998 | Schlager |
| 5,760,399 A | 6/1998 | Trygstad |
| 5,771,096 A | 6/1998 | Andersen |
| 5,781,289 A | 7/1998 | Sabsabi et al. |
| 5,799,231 A | 8/1998 | Gates et al. |
| 5,828,492 A | 10/1998 | Moser et al. |
| 5,831,742 A | 11/1998 | Watson et al. |
| 5,905,571 A | 5/1999 | Butler et al. |
| 5,939,717 A | 8/1999 | Mullins |
| 5,941,821 A | 8/1999 | Chou |
| 5,945,676 A | 8/1999 | Khalil et al. |
| 5,946,088 A | 8/1999 | Aldridge |
| 5,946,089 A | 8/1999 | Duer |
| 5,991,048 A | 11/1999 | Karlson et al. |
| 6,006,585 A | 12/1999 | Forster |
| 6,040,914 A | 3/2000 | Bortz et al. |
| 6,124,937 A | 9/2000 | Mittenzwey et al. |
| 6,137,108 A | 10/2000 | DeThomas et al. |
| 6,176,323 B1 | 1/2001 | Weirich et al. |
| 6,198,531 B1 | 3/2001 | Myrick et al. |
| 6,304,854 B1 | 10/2001 | Harris |
| 6,317,648 B1 | 11/2001 | Sleep et al. |
| 6,347,131 B1 | 2/2002 | Gusterson |
| 6,350,389 B1 | 2/2002 | Fujishima et al. |
| 6,420,708 B2 | 7/2002 | Wilks, Jr. et al. |
| 6,430,513 B1 | 8/2002 | Wang et al. |
| 6,437,326 B1 | 8/2002 | Yamate et al. |
| 6,469,785 B1 | 10/2002 | Duveneck et al. |
| 6,476,384 B1 | 11/2002 | Mullins et al. |
| 6,490,035 B1 | 12/2002 | Folestad et al. |
| 6,517,230 B1 | 2/2003 | Afnan et al. |
| 6,522,945 B2 | 2/2003 | Sleep et al. |
| 6,529,276 B1 | 3/2003 | Myrick |
| 6,573,999 B1 | 6/2003 | Yang |
| 6,600,560 B2 | 7/2003 | Mikkelsen et al. |
| 6,630,663 B2 | 10/2003 | Murphy et al. |
| 6,667,802 B2 | 12/2003 | Faus et al. |
| 6,690,464 B1 | 2/2004 | Lewis et al. |
| 6,697,195 B2 | 2/2004 | Weber et al. |
| 6,707,043 B2 | 3/2004 | Coates et al. |
| 6,711,503 B2 | 3/2004 | Haaland |
| 6,737,654 B2 | 5/2004 | Ducourant |
| 6,741,335 B2 | 5/2004 | Kinrot et al. |
| 6,748,334 B1 | 6/2004 | Perez et al. |
| 6,765,212 B2 | 7/2004 | Faus et al. |
| 6,771,369 B2 | 8/2004 | Rzasa et al. |
| 6,776,517 B2 | 8/2004 | Afnan et al. |
| 6,798,518 B2 | 9/2004 | Difoggio et al. |
| 6,853,447 B2 | 2/2005 | Goetz |
| 6,870,629 B1 | 3/2005 | Vogel et al. |
| 6,952,267 B2 | 10/2005 | Rarac |
| 6,980,285 B1 | 12/2005 | Hansen |
| 6,982,431 B2 | 1/2006 | Modlin et al. |
| 6,995,840 B2 | 2/2006 | Hagler |
| 7,006,214 B2 | 2/2006 | Rzasa et al. |
| 7,123,844 B2 | 10/2006 | Myrick |
| 7,138,156 B1 | 11/2006 | Myrick et al. |
| 7,145,145 B2 | 12/2006 | Benson |
| 7,173,239 B2 | 2/2007 | DiFoggio |
| 7,245,374 B2 | 7/2007 | Hendriks |
| 7,271,883 B2 | 9/2007 | Newell et al. |
| 7,348,493 B2 | 3/2008 | Osanai et al. |
| 7,399,968 B2 | 7/2008 | Lewis et al. |
| 7,405,825 B2 | 7/2008 | Schuurmans et al. |
| 7,411,729 B2 | 8/2008 | Lyama et al. |
| 7,569,354 B2 | 8/2009 | Okano et al. |
| 7,623,233 B2 | 11/2009 | Freese et al. |
| 7,652,767 B2 | 1/2010 | Harsh et al. |
| 7,671,973 B2 | 3/2010 | Van Beek et al. |
| 7,697,141 B2 | 4/2010 | Jones et al. |
| 7,853,104 B2 | 12/2010 | Oota et al. |
| 7,889,346 B2 | 2/2011 | Myrick et al. |
| 7,911,605 B2 | 3/2011 | Myrick et al. |
| 7,920,258 B2 | 4/2011 | Myrick et al. |
| 7,993,276 B2 | 8/2011 | Nazarian et al. |
| 2001/0034064 A1 | 10/2001 | Turner et al. |
| 2002/0005108 A1* | 1/2002 | Ludwig ..................... 84/600 |
| 2002/0008215 A1 | 1/2002 | Evans |
| 2002/0050567 A1 | 5/2002 | Boudet et al. |
| 2002/0071118 A1 | 6/2002 | Shinbori et al. |
| 2002/0108892 A1 | 8/2002 | Goetz et al. |
| 2002/0109094 A1 | 8/2002 | Goetz et al. |
| 2002/0154315 A1 | 10/2002 | Myrick |
| 2003/0056581 A1 | 3/2003 | Turner et al. |
| 2003/0059820 A1 | 3/2003 | Vo-Dinh |
| 2003/0071988 A1 | 4/2003 | Smith et al. |
| 2003/0094495 A1 | 5/2003 | Knowles et al. |
| 2003/0111606 A1 | 6/2003 | Berghmans et al. |
| 2003/0117628 A1 | 6/2003 | Harju et al. |
| 2003/0202179 A1 | 10/2003 | Larsen et al. |
| 2004/0012782 A1 | 1/2004 | Mason et al. |
| 2004/0106098 A1 | 6/2004 | Chen et al. |
| 2004/0160601 A1 | 8/2004 | Womble et al. |
| 2004/0197850 A1 | 10/2004 | Baer et al. |
| 2004/0227086 A1 | 11/2004 | Haug et al. |
| 2005/0077476 A1 | 4/2005 | Poteet et al. |
| 2005/0087132 A1 | 4/2005 | Dickey et al. |
| 2005/0167264 A1 | 8/2005 | Sternbergh et al. |
| 2005/0251289 A1 | 11/2005 | Bonney et al. |
| 2005/0264815 A1 | 12/2005 | Wechsler et al. |
| 2005/0288906 A1 | 12/2005 | Drennen, III et al. |
| 2006/0035018 A1 | 2/2006 | Sakurai et al. |
| 2006/0051036 A1 | 3/2006 | Treado et al. |
| 2006/0093523 A1 | 5/2006 | Norman |
| 2006/0142955 A1 | 6/2006 | Jones et al. |

(56) References Cited

U.S. PATENT DOCUMENTS

| | | | |
|---|---|---|---|
| 2006/0153492 | A1 | 7/2006 | Treves et al. |
| 2006/0158734 | A1 | 7/2006 | Schuurmans et al. |
| 2006/0169902 | A1 | 8/2006 | Watanabe |
| 2006/0197015 | A1 | 9/2006 | Sterling et al. |
| 2006/0276697 | A1 | 12/2006 | Demuth et al. |
| 2007/0035737 | A1 | 2/2007 | Andrews et al. |
| 2007/0137292 | A1 | 6/2007 | Xian et al. |
| 2007/0201136 | A1 | 8/2007 | Myrick |
| 2007/0282647 | A1 | 12/2007 | Freese et al. |
| 2007/0294094 | A1 | 12/2007 | Alessandrini et al. |
| 2008/0111064 | A1 | 5/2008 | Andrews et al. |
| 2008/0231849 | A1 | 9/2008 | Myrick |
| 2008/0276687 | A1 | 11/2008 | Myrick et al. |
| 2008/0309930 | A1 | 12/2008 | Rensen |
| 2009/0002697 | A1 | 1/2009 | Freese et al. |
| 2009/0015819 | A1 | 1/2009 | Van Beek et al. |
| 2009/0033933 | A1 | 2/2009 | Myrick |
| 2009/0073433 | A1 | 3/2009 | Myrick et al. |
| 2009/0097024 | A1 | 4/2009 | Blackburn et al. |
| 2009/0140144 | A1 | 6/2009 | Myrick et al. |
| 2009/0216504 | A1 | 8/2009 | Priore et al. |
| 2009/0219538 | A1 | 9/2009 | Myrick et al. |
| 2009/0250613 | A1 | 10/2009 | Myrick et al. |
| 2009/0299946 | A1 | 12/2009 | Myrick et al. |
| 2009/0316150 | A1 | 12/2009 | Myrick et al. |
| 2010/0042348 | A1* | 2/2010 | Bakker ............................ 702/85 |
| 2010/0073666 | A1 | 3/2010 | Perkins et al. |
| 2010/0141952 | A1 | 6/2010 | Myrick et al. |
| 2010/0149537 | A1 | 6/2010 | Myrick et al. |
| 2010/0153048 | A1 | 6/2010 | Myrick et al. |
| 2010/0182600 | A1 | 7/2010 | Freese et al. |
| 2010/0195105 | A1 | 8/2010 | Myrick et al. |
| 2010/0211329 | A1 | 8/2010 | Farquharson et al. |
| 2010/0245096 | A1 | 9/2010 | Jones et al. |
| 2010/0265509 | A1 | 10/2010 | Jones et al. |
| 2010/0302539 | A1 | 12/2010 | Myrick et al. |
| 2010/0305741 | A1 | 12/2010 | Myrick |
| 2010/0328669 | A1 | 12/2010 | Myrick et al. |

FOREIGN PATENT DOCUMENTS

| | | | |
|---|---|---|---|
| EP | 1974201 | A1 | 10/2008 |
| EP | 2087328 | A2 | 8/2009 |
| EP | 2140238 | A1 | 1/2010 |
| JP | 57142546 | A | 9/1982 |
| JP | 4001558 | A | 1/1992 |
| JP | 07-053582 | B2 | 6/1996 |
| JP | 11506206 | | 6/1996 |
| JP | 9-3662 | | 1/1997 |
| JP | 11506207 | | 6/1999 |
| WO | 96/30746 | | 10/1996 |
| WO | 2004/057284 | A1 | 7/2004 |
| WO | 2005/062006 | A1 | 7/2005 |
| WO | 2005/062986 | A2 | 7/2005 |
| WO | WO 2005/062986 | | 7/2005 |
| WO | 2006/031733 | A2 | 3/2006 |
| WO | 2006/064446 | A1 | 6/2006 |
| WO | 2006/137902 | A2 | 12/2006 |
| WO | 2007/061435 | A1 | 5/2007 |
| WO | 2007/061436 | A1 | 5/2007 |
| WO | 2007/061437 | A1 | 5/2007 |
| WO | 2007/062202 | A1 | 5/2007 |
| WO | 2007/062224 | A1 | 5/2007 |
| WO | 2007/064578 | A2 | 6/2007 |
| WO | 2008/002903 | A2 | 1/2008 |
| WO | 2008/057912 | A2 | 5/2008 |
| WO | 2008/057913 | A2 | 5/2008 |
| WO | 2008/121684 | A1 | 10/2008 |

OTHER PUBLICATIONS

E.B. Martin et al., "Process Performance Monitoring Using Multivariate Statistical Process Control", IEE Proc.—Control Theory Appl., vol. 143, No. 2, pp. 132-144, Mar. 1996.

Mandelis et al., "Theory of Photopyroelectric Spectroscopy of Solids", Journal of Applied Physics, vol. 57, No. 9, pp. 4421-4430, 1985.

Zagonel et al., "Multivariate Monitoring of Soybean Oil Ethanolysis by FTIR", Talanta, vol. 63, No. 4, pp. 1021-1025, 2004.

Inon et al., "Combination of Mid- and Near-Infrared Spectroscopy for the Determination of the Quality Properties of Beers", Analytica Chimica Acta, vol. 571, No. 2, pp. 167-174, 2006.

Czarnik-Matusewicz et al., Temperature-Dependent Water Structural Transitions Examined by Near-IR and Mid-IR Spectra Analyzed by Multivariate Curve Resolution and Two-Dimensional Correlation Spectroscopy, Analytica Chimica Acta, vol. 544, No. 1-2, pp. 15-25, 2005.

Pimentel et al., "Determination of Biodiesel Content when Blended with Mineral Diesel Fuel Using Infrared Spectroscopy and Multivariate Calibration", Microchemical Journal, vol. 82, No. 2, pp. 201-206, 2006.

Ghesti et al., "Application of Raman Spectroscopy to Monitor and Quantify Ethyl Esters in Soybean Oil Transesterification", Journal of the American Oil Chemists' Society, vol. 83, pp. 597-601, 2006.

Dereniak et al., *Infrared Detectors and Systems*, John Wiley & Sons: New York, Chapter 9, pp. 395-438, 1996.

Prystay et al., "Thermophysical Measurements and Interfacial Adhesion Studies in Ultrathin Polymer Films Using Homodyne Photothermal Spectrometry", Applied Spectroscopy, vol. 47, No. 4, pp. 501-514, 1993.

Simcock et al, "Tuning D* with Modified Thermal Detectors", Applied Spectroscopy, vol. 60, No. 12, pp. 1469-1476, 2006.

Lang, "Ferroelectric Polymers and Ceramic-Polymer Composites", Key Engineering Materials, vol. 92-93, pp. 83-142, 1994.

Profeta et al., "Spectral Resolution in Multivariate Optical Computing", Spectrochimica Acta Part A: Molecular and Biomolecular Spectroscopy, vol. 67, pp. 483-502, 2007.

Power et al., "Rapid Recovery of Wide Bandwidth Photothermal Signals via Homodyne Photothermal Spectrometry: Theory and Methodology", Applied Spectroscopy, vol. 47, No. 4, pp. 489-500, 1993.

Workman, Handbook of Organic Compounds: NIR, IR, Raman and UV-Vis Spectra Featuring Polymers and Surfactants (a 3-volume set); Academic Press: San Diego, vol. 3, pp. 96-160, 2001.

Knothe, "Analyzing Biodiesel: Standards and Other Methods", Journal of the American Oil Chemists Society, vol. 83, No. 10, pp. 823-833, 2006.

E.D. Palik, *Handbook of Optical Constants of Solids I*, Academic Press, San Diego, pp. 350-357, 1998.

M.L. Myrick, "Multivariate optical elements simplify spectroscopy", Laser Focus World 38, 91-94, 2002.

O. Soyemi et al., "Design and testing of a multivariate optical element: The first demonstration of multivariate optical computing for predictive spectroscopy", Anal. Chem. 73, No. 6, pp. 1069-1079, (2001).

M.L. Myrick et al., "A single-element all-optical approach to chemometric prediction", Vib. Spectrosc. 28, 73-81, 2002.

A.M.C. Prakash et al., "Optical regression: a method for improving quantitative precision of multivariate prediction with single channel spectrometers", Chemom. Intell. Lab. Syst. 46, 265-274, 1999.

R.A. Deverse et al., "Realization of the Hadamard multiplex advantage using a programmable optical mask in a dispersive flat-field near-infrared spectrometer", Appl. Spectrosc. 54, 1751-1758, 2000.

F.G. Haibach et al., "Precision in multivariate optical computing", Appl. Optics 43, 2130-2140, 2004.

M.L. Myrick et al., "Application of multivariate optical computing to simple near-infrared point measurements", Proceedings of the SPIE, Bellingham, VA, US, vol. 4574, pp. 208-215, 2002.

O.S. Heavens, *Optical Properties of Thin Solid Films*, Dover Publications, Inc., Mineola, USA, pp. 62-81, 242-249, 1991.

S. Betancourt et al., "Analyzing Hydrocarbons in the Borehole", Oilfield Review, pp. 54-61, Autumn 2003.

D. Eastwood et al., "Field applications of stand-off sensing using visible/NIR multivariate optical computing", Ground and Air Pollution Monitoring and Remediation, SPIE vol. 4199, pp. 105-114, 2001.

(56) References Cited

OTHER PUBLICATIONS

Haibach et al., "On-line Reoptimization of Filter Designs for Multivariate Optical Elements", Applied Optics, vol. 42, No. 10, pp. 1833-1838, Apr. 1, 2003.
Mullins et al., "Gas-Oil Ratio of Live Crude Oils Determined by Near-Infrared Spectroscopy", Optical Methods for Industrial Processes, Proceedings of SPIE vol. 4201, pp. 73-81, 2001.
M.P. Nelson et al., "Multivariate optical computation for predictive spectroscopy", SPIE Vo. 3261, pp. 232-243, 1998.
O. Soyemi et al., "A Simple Optical Computing Device for Chemical Analysis", Proceedings of SPIE Vo. 4284, pp. 17-28, 2001.
O. Soyemi et al., "Design of angle tolerant multivariate optical elements for chemical imaging", Applied Optics, vol. 41, No. 10, pp. 1936-1941, Apr. 1, 2002.
O. Soyemi et al., "Nonlinear Optimization Algorithm for Multivariate Optical Element Design", Applied Spectroscopy, vol. 56, No. 4, pp. 477-487, 2002.
O. Soyemi et al., "Novel Filter Design Algorithm for Multivariate Optical Computing", Advanced Environmental and Chemical Sensing Technology, Proceedings of SPIE Vo. 4205, pp. 288-299, 2001.
Strausz et al., "About the Colloidal Nature of Asphaltenes and the MW of Covalent Monomeric Units", American Chemical Society, Energy and Fuels 16, No. 4, pp. 809-822, 2002 (abstract).
N. Aske et al., "Determination of Saturate, Aromatic, Resin, and Asphitenic (SARA) Components in Crude Oils by Means of Infrared and Near-Infrared Spectroscopy", American Chemical Society, Energy and Fuels 15, No. 5, pp. 1304-1312, 2001.
N. Aske et al., "Asphaltene Aggregation from Crude Oils and Models Systems Studied by High-Pressure NIR Spectroscopy", Energy and Fuels, American Chemical Society, 16, No. 5, pp. 1287-1295, 2002.
Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, 1998.
Y. Yan et al. "Fluorescence Fingerprint of Waters: Excitation-Emission Matrix Spectroscopy as a Tracking Tool", Applied Spectroscopy, vol. 54, No. 10, pp. 1539-1542, 2000.
M.P. Nelson et al., "Multivariate optical computation for predictive spectroscopy", Analytical Chemistry, vol. 70, No. 1, pp. 73-82, Jan. 1, 1998.
M.P. Nelson et al., "Fabrication and evaluation of a dimension-reduction fiberoptic system for chemical imaging applications", Review of Scientific Instruments, vol. 70, No. 6, pp. 2836-2843, Jun. 1999.
M.L. Myrick, "New approaches to implementing predictive spectroscopy", Proceedings of the SPIE Conference on Pattern Recognition, Chemometrics, and Imaging for Optical Environmental Monitoring, SPIE vol. 3854, pp. 98-102, Sep. 1999.
M. Groner et al., "Identification of Major Water-Soluble Fluorescent Components of Some Petrochemicals", Marine Pollution Bulletin, vol. 42, No. 10, pp. 935-941, 2001.
M.V. Schiza et al., "Use of a 2D to 1D Dimension Reduction Fiber-Optic Array for Multiwavelength Imaging Sensors", Applied Spectroscopy, vol. 55, No. 2, pp. 217-226, 2001.
M.L. Myrick et al., "Spectral tolerance determination for multivariate optical element design", Fresenius J Anal Chem, 369:351-355, 2001.
R.J. Priore et al., "Miniature Stereo Spectral Imaging System for Multivariate Optical Computing", Applied Spectroscopy, vol. 58, No. 7, pp. 870-873, 2004.
M.L. Myrick et al., "Use of Molecular Symmetry to Describe Pauli Principle Effects on the Vibration-Rotation Spectroscopy of $CO_2(g)$", Journal of Chemical Education, vol. 81, No. 3, pp. 379-382, Mar. 2004.
M.N. Simcock et al., "Precision in imaging multivariate optical computing", Applied Optics, vol. 46., No. 7, pp. 1066-1080, Mar. 1, 2007.
Ozturk et al., "Filtering Characteristics of Hybrid Integrated Polymer and Compound Semiconductor Waveguides", In: Journal of Lightwave Technology, vol. 20, No. 8, pp. 1530-1536, Aug. 2002.
P.G. Miney et al., "A New Optically Reflective Thin Layer Electrode (ORTLE) Window: Gold on a Thin Porous Alumina Film Used to Observe the Onset of Water Reduction", Electroanalysis, 16, No. 1-2, pp. 113-119, 2004.
Mullins et al., "Gas-Oil Ratio of Live Crude Oils Determined by Near-Infrared Spectroscopy", Applied Spectroscopy, vol. 55, No. 2, pp. 197-201, 2001.
Dobrowolski, J.A., et al., "Refinement of Optical Multilayer Systems With Different Optimization Procedures," Applied Optics, vol. 29, No. 9, Jul. 1, 1990, pp. 2876-2893.
Sullivan, Brian T., et al., "Implementation of a Numerical Needle Method for Thin-Film Design," Applied Optics, vol. 35, No. 28, Oct. 1996, pp. 5484-5492.
The Chemistry of Ferric Chloride; Printmaking Today, vol. 4, No. 2, 1995; Cello Press Ltd., Oxon, UK, 2 pages.
MSDS Hyper Glossary is a website http://www.ilpi.com/msds/ref/index.html , Safety Emporium Laboratory and Safety Supplies, retrieved on Feb. 10, 2012, 4 pages.
Handbook of Polymer Coating for Electronic Chemistry and Applications, 2nd ed., 1990.
Ryabenko, A.G., et al., "An Algorithm for Constructing the Basis of Optimal Linear Combinations . . . " , Pattern Recognition and image Analysis, vol. 3, No. 1, 1993, 12 pages.
Moravskii, A.P., "Spectrophotometrtc Determination of the Yield of the $C_{60}$ and $C_{70}$ Fullerenes in Electric Arc Synthesis under Helium", Journal of Analytical Chemistry, vol. 53, No. 12, 1998, 8 pages.
MSDS No. F1080, Material Safety Data Sheet, Mallinckrodt Baker, Inc., Feb. 18, 2003, 6 pages.
Vasil'Ev, G.K., et al., "Rotational and Vibrational Deactivation of Excited HF Molecules", Soy. Physics-JETP, vol. 41, No. 4, 1976, pp. 617-621.
Ryabenko, A.G., et al., "Numerical Study of a Pattern Recognition Multispectral System With Optimal Spectral Splitting," Pattern Recognition and Image Analysis, vol. 1, No. 3, 1991, 10 pages.

* cited by examiner

DATA VALIDATION AND CLASSIFICATION IN OPTICAL ANALYSIS SYSTEMS

CROSS-REFERENCE TO RELATED APPLICATIONS

This application claims the benefit of U.S. Provisional Patent Application Ser. No. 60/816,461, filed Jun. 26, 2006.

FIELD OF THE INVENTION

The present invention relates to improvements related to system design, fabrication and operation of measurement systems. More particularly, the invention relates to data analysis for improved performance of multivariate optical computing systems.

BACKGROUND OF THE INVENTION

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \qquad \text{(``Equation 1'')}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the nth component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes xn of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y = a_0 + a_1 x_1 + a_2 x_2 + a_3 x_3 + a_4 x_4 \quad \text{("Equation 2")}$$

where y is octane rating, an are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength.

The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$, by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant an corresponding to the component vector, and if the resulting weighted principal components are summed by wavelength, the regression vector takes the following form:

$$y = a_0 + b_1 u_1 + b_2 u_2 + \ldots + b_n u \quad \text{("Equation 3")}$$

where y is octane rating, $a_0$ is the first regression constant from Equation 2, $b_n$ is the sum of the multiple of each regression constant an from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multi-wavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or coadds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

While various methodologies have been developed to enhance measurement accuracy in Optical Analysis Systems, the industry requires a system in which the spectral range of the illumination source can be controlled; in which light can be shined directly onto a sample with or without fiber optic probes; and in which the reflected or transmitted light can be analyzed in real time or near real time.

SUMMARY OF THE INVENTION

A method of classifying measurement results in a multivariate optical computing system can comprise receiving a first signal based on light that has interacted with a material of interest and at least one spectral element. The method can also comprise receiving a second signal based on light that has interacted with the material of interest. For instance, light may be transmitted through and/or reflected from a sample of a chemical, compound, or mixture in any suitable form or forms. The light may split, with at least a portion of the light directed through a spectral element, such as a multivariate optical element, and then into a detector. The other portion or portions of the light may be directed into a detector without first passing through a multivariate optical element in some embodiments. The multivariate optical element may, for example, perform a dot product operation on the light received from the material of interest and a weighted regression vector.

The signals may be provided to at least one computing device by one or more detectors, with the computing device(s) configured to analyze the signals in one or more ways. In some embodiments, the first and second signals may be adjusted prior to receipt and/or analysis. For example, a gain mechanism may be used to fine-tune or amplify either or both signals.

The computing device(s) can comprise any suitable number or combination of components configured to analyze signals and provide a result or results. For example, the device(s) may comprise general-purpose or specialized computer(s), controllers, or other hardware adapted to perform spectroscopic analysis. The computing device(s) may be adapted using hardware and/or software that configures the device(s) to perform steps, tasks, or processes. For instance, in some embodiments, the computing device(s) may be configured by a first software routine and/or by hardware to evaluate one or more characteristics of a material based on the values of the first and second signals. As was noted above, the characteristics may be inferred from information obtained from light that has interacted with the material, with the information of interest obtained from the light through the use of one or more spectral elements, such as a multivariate optical element or elements.

Of course, evaluation of a desired property can occur by using hardware, such as amplifiers, addition, subtraction, and other logic circuitry constructed to provide output based on the values of the signals. Thus, the term "computing device" is not meant to include only computers that operate based on software, but also circuits constructed and configured to provide output based on input signal values.

A second software routine and/or additional hardware included in or functioning in conjunction with the multivariate optical computing system can be used to validate and/or classify measurements based on the first and second signals. While validating/classifying may be advantageous when provided alongside a substantive measurement, it will be understood that validation/classification can occur without providing a measurement.

For instance, the method can further comprise providing classifying information based on determining whether the first signal and lie in a range of expected results. For example, the method can comprise accessing validation data that indicates the range of expected results. For instance, in some embodiments, the validation data comprises data indicating at least one boundary that defines expected results as a function of the values of the first and second signals. Thus, the relationship between the first and second signals can be used as a basis for classifying measurements. For example, providing classifying information can comprise determining where a given pair of simultaneous values for the first and second signal lie relative to the boundary or boundaries indicated in the validation data. Providing may further comprise storing data representing some or all of the classification data and/or generating one or more indicators of the classification data.

Alternatively, one or more circuits can be configured to provide an output or outputs based on the first and second signals, with circuit(s) configured so that the output indicates whether the first and second signals lie in an expected range of results.

In some embodiments, providing classifying information can comprise indicating whether a result is valid or invalid. For example, if validation data or a validation model comprises a two-dimensional area defined in one dimension by the value of the first signal and in the second dimension by the second signal, one or more boundaries may divide the two-dimensional area into at least valid result area and an invalid result area. Providing classifying information can comprise indicating whether a measurement is valid based on whether a data point defined by the values of the first and second signal lie in the valid result area or the invalid result data. In some embodiments, the validation data or model may comprise a plurality of boundaries defining multiple areas, such as a plurality of boundaries by confidence interval. For example, the validation data may define a first confidence interval, a second confidence interval, and a third confidence interval. Providing classification data can comprise indicating which confidence interval a particular pair of first and second signal values lies within.

An optical computing system can comprise at least one computing device adapted to: receive data from a first detector indicative of light that has interacted with a material of interest and at least one spectral element, receive data from a second detector indicative of light that has interacted with the material of interest, and produce classification data based on determining if the data from the first and second detectors lie in a range of expected results. As was noted above, a "computing device" can comprise a computer adapted by software, but may alternatively or additionally comprise circuits constructed to provide output. Similarly, detector data and classification data may comprise information in computer-readable form or may comprise analog signals.

In some embodiments, the computing device can access validation data defining the range of expected results and produce classification data based on evaluating the data from the first and second detectors and the validation data. The validation data may, for example, define at least one boundary as a function of the values of the first and second signal, and producing classification data can comprise determining where a pair of first and second signals lie relative to the boundary.

In some embodiments, the optical computing system can further comprise at least one light source configured to illuminate a material of interest and first and second broadband detectors. Each detector can be configured to detect light over a range of wavelengths and to provide data to the computing device. For example, if the computing device comprises a computer, the data may be digital. If the computing device comprises an evaluation circuit, the data may comprise one or more signals from each detector.

Embodiments of a method of configuring a measurement system can include obtaining calibration data. For example, the calibration data can comprise a plurality of data points defining a response of an optical measurement system when the system is used to measure a known type or types of material. Based on the calibration data, one or more multivariate optical elements can be constructed. Based on the data points, a validation model comprising at least one boundary can be prepared. For example, the data points may be subjected to one or more different statistical analyses to define confidence intervals. For example, a model may simply define a first confidence interval indicating valid, or expected, results and a second confidence intervals indicating invalid, or unexpected, results. As another example, a model may define multiple confidence intervals, such as 99%, 95%, 90%, or any other lower percentage values. The confidence intervals alternatively may be defined as first, second, third, fourth, fifth, and so on standard deviations (sigma).

The one or more multivariate optical elements constructed based on the calibration data can be included in a measurement system. For example, the multivariate optical elements may be placed into an optical computing system used to measure one or more characteristics of a material, or may be provided to an end-user for such placement. The calibration model may also be used to configure the measurement system to validate or classify the results. For example, a computer system associated with the measurement system may be configured to validate or classify measurements using the calibration model. As another example, circuitry included within or for use with the measurement system can be configured to validate results based on the model.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE DISCLOSURE

Figure 1:
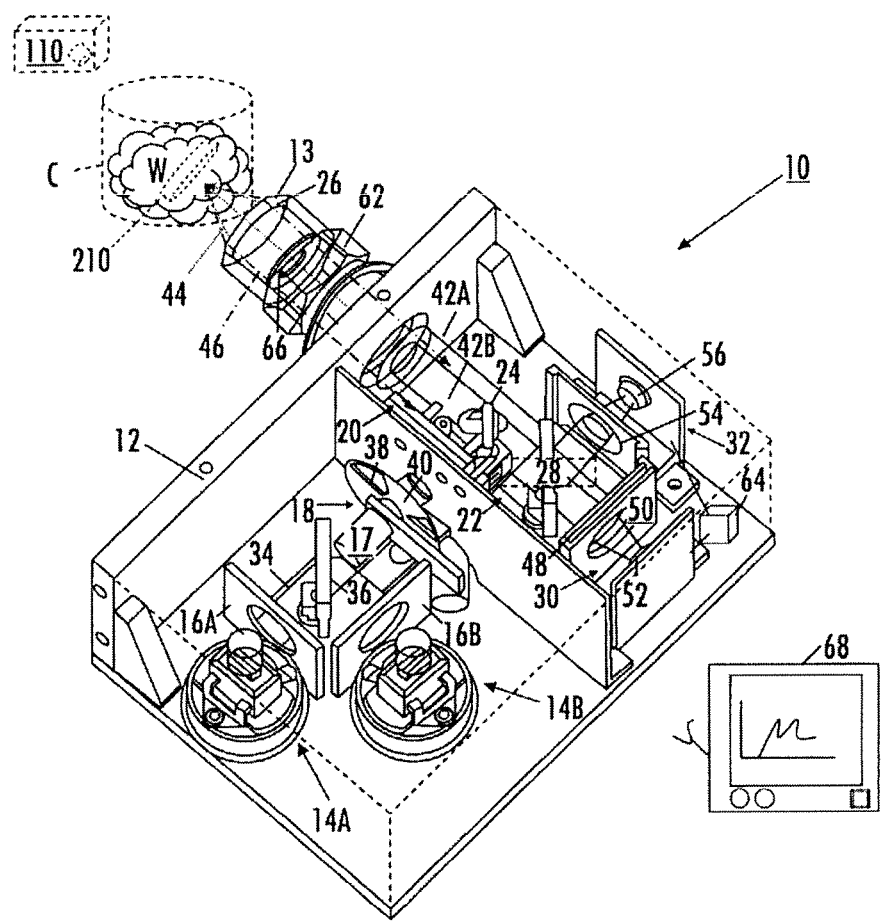
FIG. 1 is a top perspective view of one embodiment of a real time measurement system according to an aspect of the present invention.

Detailed reference will now be made to the drawings in which examples embodying the present invention are shown. The detailed description uses numerical and letter designations to refer to features of the drawings. Like or similar designations of the drawings and description have been used to refer to like or similar parts of the invention.

The drawings and detailed description provide a full and written description of the invention, and of the manner and process of making and using it, so as to enable one skilled in the pertinent art to make and use it, as well as the best mode of carrying out the invention. However, the examples set forth in the drawings and detailed description are provided by way of explanation only and are not meant as limitations of the invention. The present invention thus includes any modifications and variations of the following examples as come within the scope of the appended claims and their equivalents.

Figure 2:
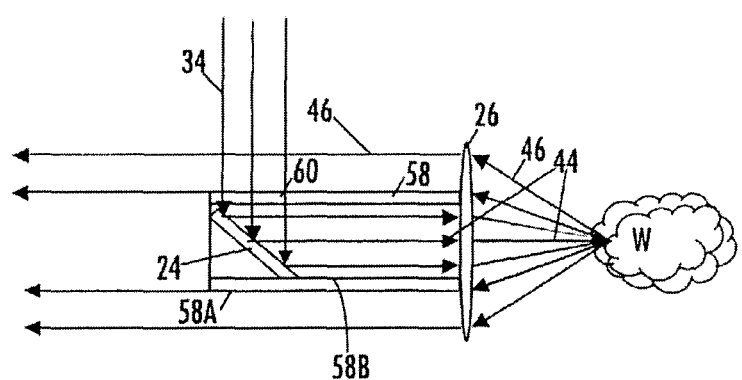
FIG. 2 is a schematic view of a concentric cavity as in FIG. 1 in accordance with a further aspect of the present invention.

As generally shown in FIGS. 1 and 2, an optical analysis system according to an aspect of the invention is designated by the element number 10. The system 10 is designed around at least one application specific multivariate optical element (MOE) based on spectra typically provided by an end-user. System design takes into account representative spectra of compounds of interest, basic and expected concentrations of interest across a range of expected interferents. Also, the system 10 incorporates the desired spectral regions (UV, VIS, NIR, MIR, IR) of interest.

In the embodiment shown in FIG. 1, the optical analysis system 10 broadly includes a housing 12, a plurality of illumination or light sources 14A, 14B, a concentric light tube or cavity 22, a focusing lens 26, at least one beam splitter 28, a first detector 30 including a multivariate optical element 48 and a second detector 32. Although FIG. 1 shows a generally square- or rectangle-shaped, metallic housing 12 and two detectors 30, 32 arranged therein, a variety of shapes, dimensions, component placements and material makeup of the components can be substituted for the examples shown according to various requirements such as government regulations, customer specifications and the like.

As used herein, the term "light" is broadly used to mean any form of radiation or radiative energy including, for instance, visible light or light in the infrared region. "Light" is also referred to herein as a light signal, a light beam, a light ray and the like to mean any form of radiative energy in the electromagnetic spectrum. Similarly, the term "transmission" can mean transmission of radiative energy onto a surface of a sample; penetration, however slight, into a sample such as a particulate sample or opaque fluid sample; or passage through a sample.

Moreover, as discussed below with respect to another embodiment of the invention, a workpiece or sample W can be analyzed using a PCR-type model without the beamsplitter 28 in an off-line approach. As used herein, the workpiece or sample W can mean an analyte undergoing analysis over a range of conditions. The sample can be a solid or a fluid including but not limited to a powder, a pharmaceutical powder mixed with lactose and other excipient materials, a chemical, a polymer, a petroleum product, a solution, a dispersion, an emulsion and combinations of these solids and fluids.

The skilled artisan will also understand that although the system can be a measurement system operating in reflectance mode, the system can also be configured to operate in a transmission mode in which light is shone through the sample W from an incident side of the sample W to a similar detection system 110 on another side of the sample W. Alternatively, or additionally, a mirrored surface 210 can be placed within the transmissive sample to reflect the light back into the detection system 10. Therefore, the invention is not limited only to the examples shown in the figures.

With more particular reference to FIG. 1, the housing 12 (shown partially in phantom for clarity) can be metal such as stainless steel, a plastic material such as high-density polyethylene (HDPE) or any durable material for protecting the components of the optical analysis system 10. As shown, sampling of the sample W is accomplished through a window 13 in the enclosed optical analysis system 10. Accordingly, the enclosed optical analysis system 10 can be used in a dangerous (e.g., explosive) environment. As will be described in detail below, the window 13 is transmissive in a known manner in a spectral region of interest.

As briefly introduced above, the illumination sources 14A, 14B are chosen to provide a source light 34, which has a spectral range determined by a spectral range of interest for the intended sample measurement. The illumination sources 14A, 14B are also chosen based on reliability, intensity, temperature generation, and other factors. The illumination sources 14A, 14B are also redundant to further enhance reliability. As shown in FIG. 1, the redundant illumination sources 14A, 14B can be oriented at 90 degrees from each other with a "50-50" beam splitter 36 located near their center point to provide a constant source of illumination.

FIG. 1 further shows a plurality of lenses 16A, 16B, respectively associated with each of the illumination sources 14A, 14B. The lenses 16A, 16B are used to collect the light signal 34 from the illumination sources 14A, 14B and to focus the light signal 34 on a modulator or chopper wheel 18, described below. As shown, the lenses 16A, 16B are positioned to capture as much of the light signal 34 as possible from the illumination sources 14A, 14B. Additionally, a chopper-focusing lens 17 is used to focus as much of the light signal 34 as possible through the chopper wheel 18. The lenses 16A, 16B, 17 are selected for focal length, position, material of construction and the like to enhance transmission (reduce loss) of the light signal 34. For example, in the design of the optical path, if the illumination sources 14A, 14B is a lamp, slight magnification or demagnification of the source is generally obtained at the sample W, depending on the ratios of the focal length, e.g., of the lens 16A to that placed after the illumination source 14A to collimate it. Ultimately, the image of the illumination source 14A on the sample W is directed toward the detectors 30, 32 as described below and again with some slight magnification or demagnification, depending on the ratios of the focal length, e.g., of the lenses 16A to that of, e.g., a lens 50 placed before the detector 30 to focus a reflected light 46 onto the detector 30. Thus, it should be understood that there is a relationship between the focal lengths of the lenses 16A, 16B that must be maintained in order to make sure the ultimate image of the source-excited region of the sample W that is formed on the detectors 30,32 is suited to the physical dimensions of the detectors 30,32.

Lenses 16A, 16B shown for example in FIG. 1 are plastic, Fresnel lenses well suited for use in an infrared (IR) region of about 1000 nanometers (nm) to about 3000 nm. However, the lenses 16A, 16B are not limited to only plastic, Fresnel lenses and other types of lenses and materials, such as glass or other materials, can be used for these lenses.

As further shown in FIG. 1, the chopper wheel 18 includes a plurality of alternating windows 38 and a plurality of alternating spokes 40. The alternating windows 38 and spokes 40 modulate the light signal 34 from about 50 Hertz (Hz) to about 5000 Hz to enable a plurality of photodetectors 52, 56 in the optical system 10 to perform properly, as will be further described below. As shown in this example, the chopper wheel 18 is a 10-window chopper wheel rotating at 40 Hz, which provides a chopped signal of 400 Hz. The number and arrangement of the windows 38 and spokes 40 and thus, the chopper frequency, are chosen based on several variables, including a rate of motion of the sample material W moving past the sampling window 13; a performance characteristic of the photodetectors 52,56 and amplification system; a predetermined sampling rate of the data collection and analysis system 10; physical properties of a chopper motor (not shown), control system (not shown), and the chopper wheel 18 (including material(s) of the windows 38).

More particularly, the number of windows 38 in the chopper wheel 18 can be adjusted to provide a suitable degree of signal modulation. In one aspect of the invention, the chopper wheel 18 has open windows 38 and black spokes 40, which block the light signal 34. In another aspect, different materials can be placed in the windows 38 to provide different spectral characteristics for the various windows 38. Moreover, the transmission characteristic of these windows 38 could be used as further spectral elements. The windows 38 can also contain multivariate optical elements (MOE) such as those described below with respect to a MOE 48 of the MOE detector 30.

FIG. 1 also shows a plurality of bandpass filters or spectral elements 20 located in a path of the light signal 34 after the light signal 34 has passed through the chopper wheel 18. As briefly discussed above, the spectral elements 20 are selected based on a desired application; i.e., to analyze a particular sample W. The spectral elements 20 are chosen so that the spectral region of illumination covers the desired range; i.e., related to a particular chemical material of interest. For example, if 1500-2000 nanometers (nm) of light wavelengths is the desired spectral region, the spectral elements 20 are selected to filter out wavelengths are not in that region. An example of these spectral elements is a Schott brand filter, which can be a long pass, short pass, or band pass filter. By way of further example but not of limitation, some suitable materials for use as the spectral elements 20 are listed in the following table.

With reference now to FIGS. 1 and 2, the light signal 34 exits the spectral elements 20 and reflects off a first mirror or turning mirror 24. It will be appreciated that although the turning mirror 24 is shown at an angle of about 45 degrees with the light signal 34 reflecting at this angle, the turning mirror 24 can be turned to any desired angle. The turning mirror 24 can be a powered turning mirror powered by a battery, by electricity or the like. Further description of power sources and implementation with the turning mirror 24 is not necessary for one skilled in the art to understand this aspect of the invention. Although the turning mirror 24 is shown as a unitary mirror, other embodiments can utilize multiple mirrors arranged in or adjustable to a variety of positions.

As further shown in FIGS. 1 and 2, the filtered and reflected light signal 34 becomes a reflected light 44 after being reflected by the turning mirror 24. The reflected light 44 thus continues down the concentric sampling tube 22, briefly introduced above, in a direction of the sample W. As shown and further described below, the concentric tube 22 includes an inner annular region (also referred to as tube or chamber) 42A and an outer annular region 42B (also, tube or chamber). In this example, the reflected light 44 is reflected along the inner annular region 42A. It will be understood that the illumination sources 14A, 14B and the detectors 30, 32 are shown in an exemplary orientation and can be reversed. It will be further appreciated that the light signal 34 and the reflected light 44 are shown collimated for simplicity. However, the light signal 34 and the reflected light 44 may not be com-

TABLE 1

Properties of Select Transmitting Materials

| Material | Comments | SWL cm − 1 | LWL cm − 1 | RI | Solubility g/100 g | Hardness Kg/mm 2 | MP ° C. | pH Range |
|---|---|---|---|---|---|---|---|---|
| AMTIR | SeAsGe glass, brittle | 11000 | 593 | 2.5 | 0 | 170 | 370 | 1-9 |
| $BaF_2$ | Barium Fluoride | 66600 | 691 | 1.45 | 0.17 | 82 | 1280 | 5-8 |
| $Ca F_2$ | Calcium Fluoride | 79500 | 896 | 1.4 | 0.0017 | 158 | 1360 | 5-8 |
| CsI | Cesium Iodide, very hygroscopic, Somewhat Toxic | 42000 | 172 | 1.73 | 44 | 20 | 621 | NA |
| Diamond | Type IIa, strong IR absorbance between 2700-1800 cm − 1, costly | 30000 | <2 | 2.4 | 0 | 5700 | 550 fp | 1-14 |
| Ge | Germanium, brittle, becomes opaque at elevated temperatures | 5500 | 432 | 4 | 0 | 780 | 936 | 1-14 |
| KBr | Potassium Bromide, most widely used for mid-IR applications | 48800 | 345 | 1.52 | 53 | 6 | 730 | NA |
| KCl | Potassium Chloride | 55600 | 385 | 1.45 | 35 | 7 | 776 | NA |
| KRS-5 | Thallium Bromide/ Thallium Iodide, Extremely Toxic! | 17900 | 204 | 2.37 | 0.05 | 40 | 414 | 5-8 |
| NaCl | Sodium Chloride | 52600 | 457 | 1.49 | 36 | 18 | 801 | NA |
| Polyethylene | For Far-IR, swells with some organic solvents | 625 | <4 | 1.52 | 0 | | 110 | 1.5-14 |
| $SiO_2$ | Silicon Dioxide | 50000 | 2315 | 1.53 | 0 | 460 | 1713 | 1-14 |
| Si | Silicon, strong IR absorbance between 624-590 cm − 1 | 8900 | 624.30 | 3.41 | 0 | 1150 | 1420 | 1-12 |
| ZnS | Zinc Sulfide | 17000 | 690 | 2.2 | 0 | 240 | 1830 | 5-9 |
| ZnSe | Zinc Selenide | 15000 | 461 | 2.4 | 0 | 120 | 1526 | 5-9 |

Note:
To convert from wavenumber (cm − 1) to wavelength (μm), divide 10,000 by the wavenumber; e.g., 5500 cm − 1 is equivalent to 1.8 μm or 1800 nm.
SWL—Shortest wavelength for transmission, 1 mm, 50% transmission
LWL—Longest wavelength for transmission, 1 mm, 50% transmission
RI—Refractive Index, at relevant wavelength
MP—Melting point
pH—negative log of hydrogen ion concentration pletely collimated because the illumination sources 14A, 14B can be extended rather than point sources.

The focusing lens 26 in FIGS. 1 and 2 is located near an end of the tube 22 proximate the sample W. As shown in this example, the end of the tube 22 is sealed with the transmissive window 13. The transmissive window 13 can be uniformly transmissive across wavelengths. To the extent it is not uniformly transmissive; the transmission characteristics of the transmissive window 13 can be taken into account for the design of the system 10 and in particular the MOE 48. This embodiment may include an additional focusing lens 66, which can be solid or have one or more apertures as shown in FIG. 1. The additional focusing lens 66 is used to focus or collimate a carrier light 46, described below, in a direction of the tube 22.

As further shown in FIGS. 1 and 2, the focusing lens 26 focuses the reflected light 44 onto, into or near the sample W via the transmissive window 13. In this example, the reflected light 44 is focused with a focal point 0-5 mm into the sample W. In addition to isolating components of the optical analysis system 10 from an external environment, the transmissive window 13 further enables a mixing vessel or container C, which is being tested/sampled into, to remain intact. As shown in this example, a one-inch (inner diameter) Swagelok® brand connector 62, available from Swagelok Corporation, Solon, Ohio, is used to connect the optical analysis system 10 to the mixing vessel C. This arrangement permits the reflected light 44 to be sent down the tube 22 (inner region 42A), interact with the material of interest W, reflect back up the tube 22 (outer region 42B), and be directed to the detectors 30, 32 as further described below.

As most clearly shown in FIG. 2, a tube 58 defines an aperture 60 for passage of the light signal 34 in a direction of the turning mirror 24. Separation of the illumination and reflection light paths or signals 44, 46 can be further defined or separated by physically separating the inner and outer regions 42A, 42B employing the tube 58. Any minimal reduction in light return of the carrier light 46 described below (caused by physical occupation of a portion of the outer region 42B by the tube 58) is offset by improvement in the amount of backscattered radiation returned to the detectors 30, 32 without encountering the sample W.

More specifically, the tube 58 is used to reduce a non-zero background measurement. The non-zero background measurement can occur in an optical system when a small amount of scattered light is returned to a detector even when no sample is present. Some of the scattered light can be reflected from a window, and some can come from the lenses themselves.

FIG. 2 shows that the tube 58 placed around the mirror 24 before the lens 26. The tube 58 reduces background signals by separating the excitation and collection light paths 34, 46 to minimize "cross-talk". As shown, the tube 58 defines an aperture 60 for passage of the light signal 34 in a direction of the turning mirror 24. As further shown, a conical extension 58A of the tube 58 can be placed after the mirror 24 in a direction of the detector 30. A thickness of the tube 58 should be minimized.

Also shown in FIG. 2, the tube 58 can have specular interior and exterior surfaces as well as a highly reflective coating 58B, such as gold, applied by electrolysis deposition, evaporation or other thin film coating method. The coating 58B reflects rays 34, 46 that would ordinarily terminate at a surface of the tube 58 back into respective optical paths from which they came. An image of the illumination source 14A, 14B may be vignetted, but the "lost" light in the image is still focused to a spot within the zone illuminated by the illumination source 14A, 14B. Likewise, the returning light outside the tube 58 can be kept from being lost by traveling inside an outer tube with a specular reflecting surface (not shown, but surrounding the outer light path). This will keep light loss to a minimum while keeping the input and output paths relatively isolated from one another.

As introduced above, the reflected light 46 shown in FIGS. 1 and 2 travels back down the outer annular region 42A of the sampling tube 22, past the turning mirror 24. The light 46 reaches the beam splitter 28 (one of its operating positions shown in phantom). The beam splitter 28 divides the light 46 with a neutral or gray spectrum, sending some of the light 46 in a direction of the first or Multivariate Optical Element (MOE) detector 30 through the MOE 48, briefly introduced above, and through a first lens 50 onto the photo detector 52, also briefly introduced above. The beam splitter 28 sends some other portion of the light 46 through a second lens 54 onto the other detector 56, also briefly introduced above.

As shown in the following table by example but not of limitation, some detectors suitable for use as the detectors 52, 56 include:

TABLE 2

| Detector | Types[1] | Wave Range ($\lambda\mu$) | Detectivity $D^2$ | Cut Off Frequency ($H_z$) | Operating Temperature (K) |
|---|---|---|---|---|---|
| Pt—S | PV | 0.35-0.6 | 30 | $10^8$ | 295.0 |
| Si p-n PD | PV | 0.4-1.0 | 50 | $10^7$ | 295.0 |
| Si p-i-n PD | PV | 0.4-1.1 | 80 | $10^8$ | 295.0 |
| Si APD | PV | 0.4-0.8 | 80 | $10^{10}$ | 295.0 |
| Ge p-n PD | PV | 0.6-1.8 | 50 | $10^7$ | 295.0 |
| InSb p-n PD | PV | 3.0-6.2 | 8 | $5 \times 10^2$ | 77.0 |
| PbSnTe p-n PD | PV | 5.0-11.4 | >15-60 V/W | 10 | 77.0 |
| PbS | PC | 0.5-3.8 | 15.00 | 300 | 196.0 |
| PbSe | PC | 0.8-4.6 | 3.00 | $3 \times 10^3$ | 196.0 |
| PbTe | PC | 0.8-5.5 | 0.16 | $3 \times 10^3$ | 196.0 |
| p-InSb | PC | 2.0-6.7 | 2.00 | $2 \times 10^5$ | 77.0 |
| n-InSb | PC | 1.0-3.6 | 30.00 | $2 \times 10^6$ | 195.0 |
| PbSnTe | PC | 5.0-11.0 | 1.7 | $8 \times 10^5$ | 4.2 |
| CdHgTe | PC | 5.0-16.0 | 3.00 | $10^4$ | 4.2 |
| Ge: Au | PC | 2.0-9.5 | 0.02 | $10^4$ | 77.0 |
| Ge: Zn, Au | PC | 5.0-40.0 | 1.00 | $10^3$ | 4.2 |
| Ge: Cu | PC | 5.0-30.0 | 3.00 | $10^3$ | 4.2 |
| Si: Al | PC | 2.0-16.0 | 1.00 | $10^4$ | 27.0 |
| Si: Sb | PC | 2.0-31.5 | 1.80 | $10^4$ | 4.0 |
| ATGS | TC | 1-1000 | 0.030 | 10 | 295.0 |

TABLE 2-continued

| Detector | Types[1] | Wave Range ($\lambda\mu$) | Detectivity $D^2$ | Cut Off Frequency ($H_z$) | Operating Temperature (K) |
|---|---|---|---|---|---|
| (Ba, Sr)TiO$_3$ | TC | 1-1000 | 0.011 | 400 | 295.0 |
| Si | — | 0.2-1.1 | — | — | — |
| Ge | — | 0.4-1.8 | — | — | — |
| InAs | — | 1.0-3.8 | — | — | — |
| InGaAs | — | 0.8-3.0 | — | — | — |
| InSb | — | 1.0-7.0 | — | — | — |
| InSb (77 K) | — | 1.0-5.6 | — | — | — |
| HgCdTe (77 K) | — | 1.0-25.0 | — | — | — |

Note 1:
PV—photo transistor type; PC: photo conductive detector type; TC: pyroelectric detector type Note 2:
($10^{10}$ cmHz$^{1/2}$ W$^1$)

As further shown in FIG. 1, a gain mechanism 64 is in communication with the detectors 30, 32 and the MOE 48. The gain mechanism 64 weights a magnitude of the property of an orthogonal component of a portion of the carrier light 48 as described, for instance, by Myrick et al. in U.S. Pat. No. 6,198,531 B1 and in U.S. Pat. No. 6,529,276 B1 to Myrick, which are both incorporated herein by reference thereto. Exemplary optical computing systems are also discussed in U.S. Pat. No. 7,123,844 to Myrick, which is also incorporated by reference herein.

Also, in an additional aspect shown in FIG. 1, a system 68 using an electrochemical or chemometric model can be employed to make similar or same measurements of the light 46 reflected from the sample W as the measurements described in the foregoing embodiments. For example, system 68 may be provided using one or more computing devices, such as general-purpose computers adapted by analysis software. As another example, system 68 may comprise one or more evaluation circuits that provide a result indicative of the property (properties) of interest by manipulating the detector signals through addition, subtraction, amplification, and other circuitry. By way of example but not of limitation, the system 68 may be one as described by Myrick et al. in PCT Application Number PCT/US2004/043742, based on U.S. Provisional Application No. 60/533,570, filed Dec. 31, 2003, which are incorporated herein by reference to these applications.

As briefly introduced above, the beam splitter 28 is not required in an alternative embodiment of the invention in which a signal from the sample W is analyzed using a PCR-type model in an off-line approach. This alternative embodiment and approach is useful, for instance, for studying signals independently. More particularly, a system substantially as described above but without the beam splitter 28 is used to take an integral of the light on a detector similar to the detector 30 described above. By analyzing frequency-dependent intensities, results similar to those of the foregoing embodiment are produced, although possibly with a relatively slower response time in the present embodiment.

In addition to the reflectance mode described above, one or more optical analysis systems can operate in a transmission mode in conjunction with the foregoing embodiments. In such a case, light is directed (passes) through the sample W, e.g., a fluid sample, and collected on another side of the sample W to enable study of particle density in the fluid in conjunction with the chemical content described above. For instance, the system 10 can be configured to operate in transmission mode where the light is shone through the sample W to a similar detection system 110 as shown in FIG. 1 in phantom for clarity. Additionally, or alternatively, a mirrored surface 210 can be placed within the transmissive sample W to reflect the light back into the system 10.

Figure 3:
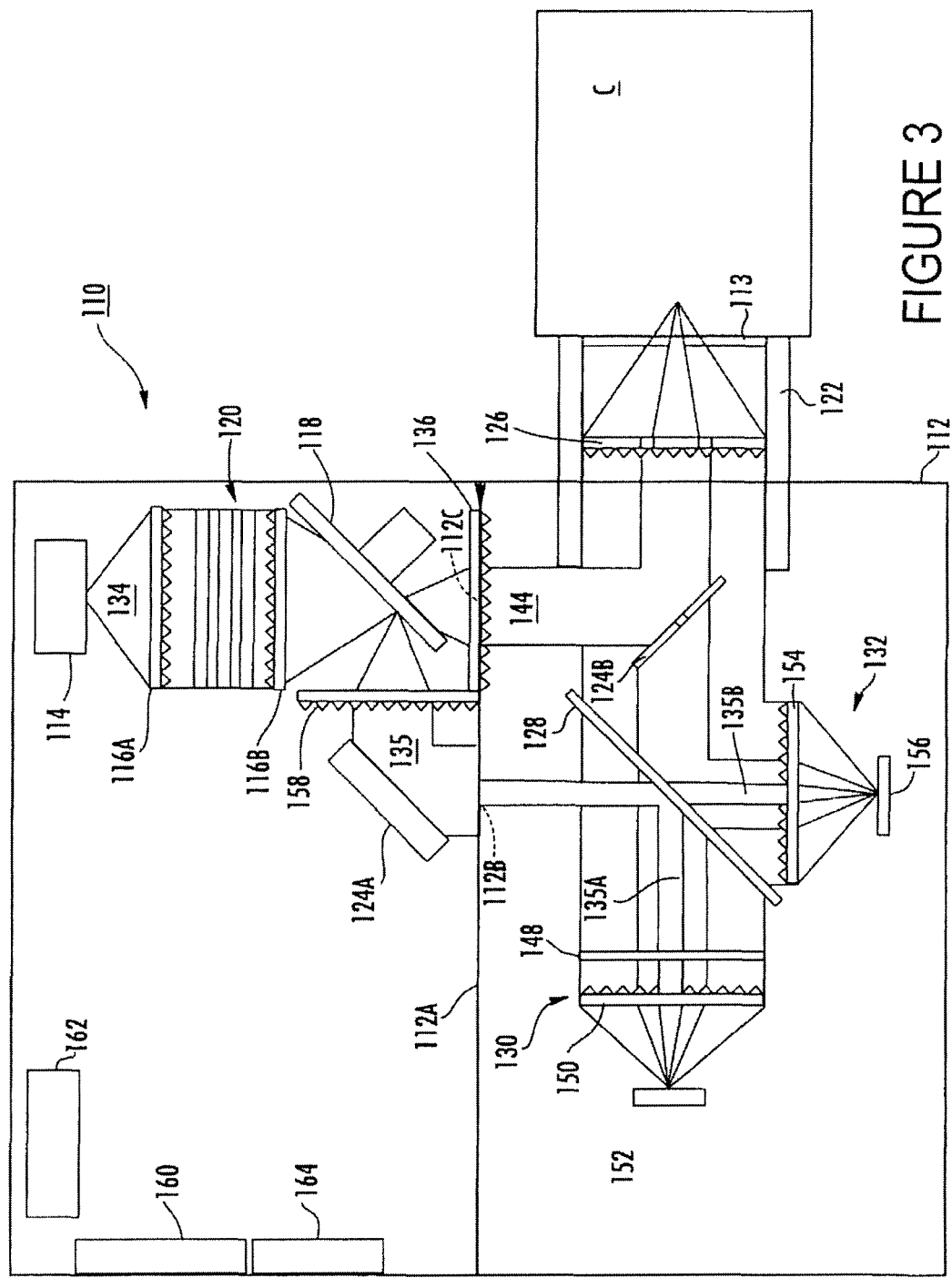
FIG. 3 is schematic plan view of another embodiment of a real time measurement system according to another aspect of the present invention.

With reference now to FIG. 3, a second exemplary embodiment of the present subject matter is designated generally by reference number 110. Many aspects of the optical analysis system 110 and related components are similar to the foregoing embodiment; thus, for the sake of brevity, only certain differences are described below. However, to provide a full and enabling disclosure of the optical analysis system 110, when like or similar elements and components are not specifically described below; implicit reference is made to the foregoing descriptions.

As shown in FIG. 3, the optical analysis system 110 broadly includes a housing 112, an illumination or light source 114, a chopper wheel 118, one or more spectral elements 120, a focusing lens 126, a beam splitter 128, a first detector 130 including a multivariate optical element 148, and a second detector 132. The optical analysis system 110 further includes an electrical connection 160, a pressurization sensor 162 and a purge gas assembly 164, which those skilled in the art will readily understand; therefore, further description is not necessary to understand and practice these aspects of the invention.

With more particular reference to FIG. 3, the illumination source 114 provides a light 134, which passes through a collecting Fresnel lens 116A and into and through the spectral element(s) 120. In this example, the illumination source 114 is rated for at least about 10,000 hours of operation, which alleviates a need for redundant illumination sources though they may be provided if desired. Also in this example, the collecting Fresnel lens 116A is sized to be about 1.5 square inches and is spaced about 0.6 inches from the illumination source 114. These dimensions can be adjusted according to particular system requirements and are not meant as limitations.

As further shown in FIG. 3, the light 134 passes through the spectral elements 120, which filter out undesired wavelengths to define a desired spectral region, e.g., 1500-2000 nm, in order to target a particular chemical material of interest. The light 134 is focused by focusing Fresnel lens 116B, which is also sized to be about 1.5 square inches and spaced about 1 inch from the chopper wheel 118. As shown, the chopper wheel 118 reflects a portion of light 134 as a calibration or reference light 135 and a transmitted light 144. Calibration light 135 is collimated by lens 158 before reflecting from a first mirror 124A through an adjustable aperture 112B in a bulkhead 112A of the housing 112. The aperture 112B is adjustable to dictate a desired amount of the calibration light 135. Finally, calibration light 135 impinges on beam splitter 128 thereby sending a portion 135A of calibration light 135 to the first MOE detector 130 and a portion 135B of calibration light 135 to the second or baseline detector 132.

FIG. 3 further illustrates that transmitted light 144 passes from the chopper wheel 118 into a collimating Fresnel lens 136, which in this example is sized to be about 1.5 square inches and is spaced about 0.6 inches from the chopper wheel 118. The transmitted light 144 passes through another adjustable aperture 112C in the bulkhead 112A and impinges upon a second mirror 124B, which directs the transmitted light 144 toward a sample in a container C, such as mixing vat or blender. The skilled artisan will recognize that the container could be a conveyor belt or other device for holding or transporting the sample and is not limited to an enclosed container.

As shown in FIG. 3, the transmitted light 144 is focused by the focusing Fresnel lens 126, which in this example may be round and about $15/16$ inches in diameter and is adjustable with an inner tube 122. Also in this example, lens 126 may be positioned about 0.6 inches from an outer surface of the container C. As shown, the transmitted light 144, now focused, passes through a transmissive window 113, which in this example is approximately 1 inch in diameter and with an anti-reflective (AR) coating disposed on one or both sides of the lens 126. The AR coating ensures that the chemical process in the container C does not interfere with the measuring process of optical analysis system 110. Thus, the transmitted light 144 enters the container C and reflects from the sample as a carrier light 146. The sample can be a moving mixture such as aspirin and an excipient being blended in real time, or a plurality of tablets passing by on a conveyor belt at high speed.

FIG. 3 further illustrates that the carrier light 146 is directed by the tube 122 in a direction of the first detector 130. Eventually, the carrier light 146 impinges on the beam splitter 128 and a portion passes in a direction of the detector 132 for baselining with the portion 135B of the calibration light 135. Another portion of the carrier light 146 passes through MOE 148, which as noted above, has been selected for the chemical of interest based on the various components of the system 110. Finally, that portion of the carrier light 146, having passed through the MOE 148, is focused by lens 150 and received by the detector 152. As described above, the two signals collected by the detectors 132 and 152 can be manipulated, e.g., mathematically, to extract and ascertain information about the sample carried by the carrier light 146.

Although exemplary embodiments of measurement systems have been described in such a way as to provide an enabling disclosure for one skilled in the art to make and use the invention, it should be understood that the descriptive examples of the invention are not intended to limit the present invention to use only as shown in the figures. For instance, the housing 16 can be shaped as a square, an oval, or in a variety of other shapes. Further, a variety of light sources can be substituted for those described above. It is intended to claim all such changes and modifications as fall within the scope of the appended claims and their equivalents. Thus, while exemplary embodiments of measurement systems have been shown and described, those skilled in the art will recognize that changes and modifications may be made to the foregoing examples without departing from the scope and spirit of the invention.

Dynamic Real-Time Detection and Measurement

The functionality of an MOC system, such as system 10 or 110 as described above, allows for the collection of the entire spectral range of testing simultaneously. This fact is notably different than either a system based on either a scanning lamp or detector system or a discrete diode array detection system. The ability to monitor over the complete spectral range of interest opens up a re-definition of the term "real-time" measurement and analysis.

For instance, true real-time process measurements are possible. "Real time" refers to obtaining data without delays attendant to collecting samples or delays due to lengthy computer processing of measurement signals. In embodiments disclosed herein, process data can be obtained in an instantaneous or near-instantaneous manner through using the disclosed measurement techniques to directly monitor materials of interest while such materials are undergoing process steps. Long delays due to processing of measurement signals are avoided by optically processing the light as it is reflected from the material(s) of interest.

Embodiments of the systems and methods disclosed herein can be utilized in analyzing solids, solutions, emulsions, gases, and dispersions, for example. In addition, while exemplary embodiments discussed herein use reflectance measurements, measurements in a transmission or transflectance mode would also be appropriate. The presently-disclosed technology can be applied to real-time measurements for a range of industrial applications. These include, but are not limited to monitoring of the blending of pharmaceutical powders, including excipients, additives, and active pharmaceutical materials; blending of other powders, including food and chemicals; monitoring dispersions and bi-phasic mixtures (such as insulin, emulsions); and oil and gas applications, including analyzing water content in oil, or oil content in water.

Inclusion of a transmissive window provides physical separation between the measuring device and the process or material being tested. Therefore, this window allows for in-line measurement and/or non-invasive measurement of parameters such as chemical functionality, including alcohol content of petroleum fractions or tackifier resins. Environmental applications are also conceivable, such as stack gas analysis, including measurement of NOx, SOx, CO, CO2, or other gases in a gas stream; wastewater analysis and treatment monitoring; and hazardous substance monitoring applications such as mercury vapor detection.

One of ordinary skill in the art will recognize that differing applications may require modifications and alterations to certain components in order to take full advantage of the presently-disclosed systems. For instance, more diffusion of light has been observed in solid powders relative to liquids; accordingly, different lenses may be needed when a liquid is monitored in order to account for such variations and achieve more accurate measurements.

Figure 4:
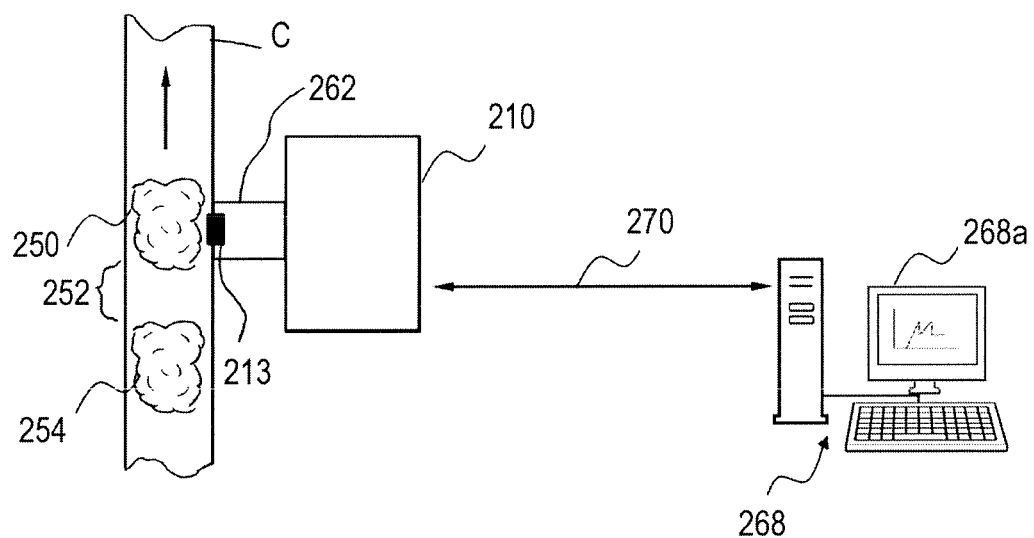
FIG. 4 is a schematic view of an exemplary implementation in which material(s) undergoing a process step may be measured in real-time using a multivariate optical computer.

FIG. 4 is a block diagram illustrating an exemplary measurement setup. In this example, a container C, which may comprise a pipe or conveyor, is used to transport one or more materials of interest. Materials in container C are shown as two generalized masses 250 and 254 with a gap 252 therebetween. For instance, gap 252 may represent the space between two samples on a conveyor or a break in continuous material. Gap 252 may represent another material, such as a gas bubble in a pipe. Of course, in other embodiments, materials may move through or occupy a container with no gaps or breaks.

Exemplary optical analysis system 210 is configured to perform optical measurements of materials therein via transmissive window 213. For example, if container C comprises a closed container, then connector 262 may be used at an opening in the container. Of course, if container C comprises an open container (e.g. a conveyor or open mixing vat), then no connector may be necessary.

Connection 270 represents the exchange of data between components of system 210 and a computing device 268, shown here as a personal computer. Screen 268a of computing device 268 may be used to provide data to one or more users, such as a technician or engineer monitoring one or more properties of a material of interest. Connection 270 may comprise any number and type(s) of connections, including wired or wireless network connections (such as Ethernet or 802.11-compliant wireless connections), serial connections, and the like. Computing device 268 may be located proximate to analysis system 210 or may be remotely connected thereto via, for example, a wide-area network such as the Internet. In other embodiments, computing device 268 need not comprise a computer, but may instead comprise one or more evaluation circuits constructed to provide output(s) indicative of the property (properties) of interest in response to the detector signal values.

An optical analysis system, such as system 10, 110, 210 as shown in FIGS. 1, 3, and 4 can be used to perform chemometric analysis to develop a correlation between characteristics of a set of spectra and a system variable. For example, a system may be used to determine the concentration of an analyte in a mixture. However, the optical computing (or chemometric) model is only as good as the data used to develop it. Using a model on a set of data that was generated and collected for a different environment can lead to spurious results. Even worse, a sample from effectively a different system could produce a system output that falls within the range of expected outputs and the concentration is erroneously reported. In some embodiments of the present subject matter, optical computing can be used to identify out-of-specification results.

For example, system 210 of FIG. 4 may be used to determine the concentration of an analyte, such as water, in a mixture, such as dog food produced by a facility. For instance, container C may represent a pipe through which dog food 250 is transferred after mixing. By using one or more multivariate optical elements, computing device 268 can provide output data including the water concentration in dog food samples. However, problems could develop if a different material moves through the pipe. For example, material 254 may represent cat food also produced by the facility. For instance, a dog food process may have ended and switched to production of cat food that is transferred using the same pipe (container C). Alternatively, a production error may result in unintentional routing of cat food 254 through container C.

Depending on the particular properties of the materials and the measured property (properties), the measurement data may be too ambiguous for a technician or other responsible person to discern the change from dog food to cat food. For example, if the optical properties of the dog food 250 and cat food 254 are very divergent, then the optical analysis system may not be able to provide any measurement at all, or may provide clearly inaccurate measurements. For instance, the expected moisture content of dog food 250 may range from 11% to 15%. If cat food 254 is measured using the system as configured for dog food, the output moisture content may be spurious enough (e.g. 0%, 100%, etc.) to indicate a problem. However, this may not always be the case.

For instance, the properties of dog food 250 and cat food 254 may be similar enough for the optical analysis system to provide output that results in an indicated moisture content falling within the expected output of 11% to 15% in this example. In any event, though, the moisture content is likely to be unreliable, since the measurement model is developed for dog food 250 and not cat food 254. Put another way, the model developed for dog food analysis may inadvertently provide erroneous output without any indication that the output is erroneous.

It is known in the art to use principal component analysis (PCA), partial least squares (PLS), and other regression methods to analyze sets of data to assess relationships within the data. One such determination is to categorize the data, even as basic as effectively saying "these data have a relationship" while "these other data do not have such a relationship." This categorization can be termed classification. This technique has been applied to data in fields such as environmental, GIS, human health, chemical analysis, and drug discovery. An important aspect in analyzing large data sets is the ability to identify spurious or outlying data that could influence the general conclusions about the data. In embodiments of the present subject matter, optical computing can be used to perform classification analysis. This classification can enable an instantaneous determination of whether a given measurement is valid.

In the examples below, signal A is the signal at the detector 52 (FIG. 1) with the Multivariate Optical Element (MOE) and signal B is the reference signal at a second detector 56 (FIG. 1). The ratio of A/B provides a referenced signal and measurement of the dependent variable of interest. Because the detectors used in this ASMOC system are broadband detectors, signals A and B are the sum of all wavelengths of that light. By analyzing signals A, B, and A/B independently, it is possible to develop additional information about the measurement and the validity of it. In particular, by analyzing the relationship between signal A and signal B, the relationship between the two can be used to define the "expected performance" and the expected range of results for the data set used to develop the model. For example, by plotting the A signal against the B signal, for a given set of data, the result in general is a line, the slope of which is a function of the MOE used to make the measurement. In addition, statistical analysis, such as mean, standard deviation, 95% confidence interval, or others, can be used to determine the range of expected results for a given model system.

However, it is emphasized that the present subject matter is not limited to any particular type or number of detectors. In the examples herein, two detector signals are used along with calibration data to classify measurements since the exemplary optical analysis systems utilize two detectors. However, other optical analysis systems may utilize three or more detectors for data classification and/or measurement purposes. Appropriate calibration and classification models can be prepared for use in such optical analysis systems in accordance with the subject matter discussed herein.

The following example is provided to illustrate the present invention and is not intended to limit the scope of the invention. Spectral data from a pharmaceutical application were analyzed for this example. There were three sets of data, from three samples of pharmaceutical material designated as Calibration, Validation 1, and Validation 2. The "Calibration" material and "Validation 1" material are similar materials, while the "Validation 2" material is a different material.

Figure 5:
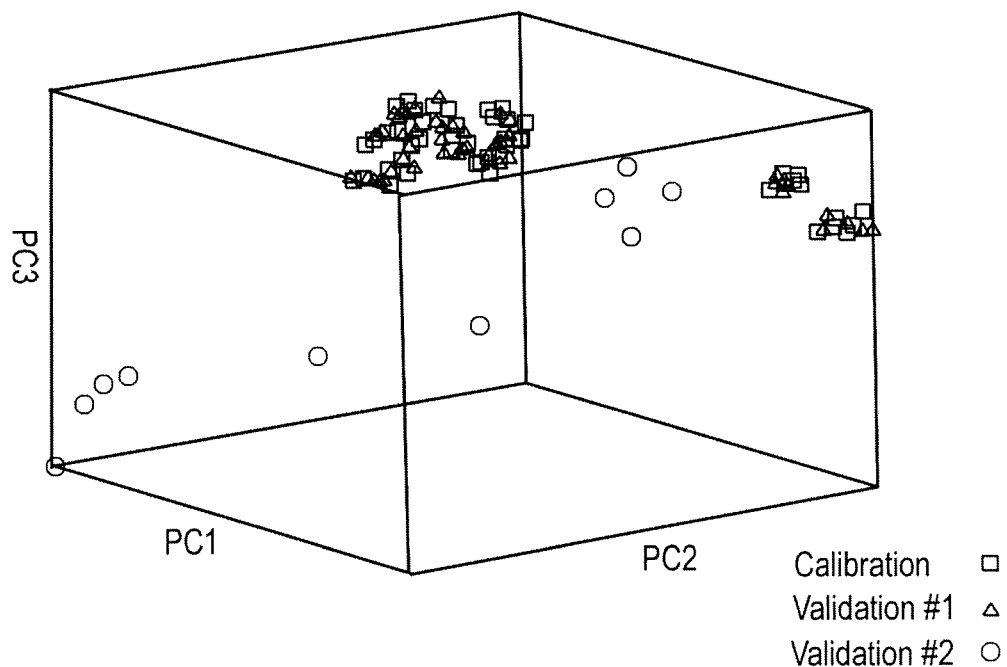
FIG. 5 is a 3-D graph of exemplary principal components for three data sets showing overlapping and outlying data points.

A single value decomposition (SVD) was performed on the Calibration data and regression vectors were calculated retaining varying numbers of principal components. For each of the first three principal components, the dot product of the calculated regression vector with the spectra is plotted in FIG. 5 in an x-y-z graph. The squares are the Calibration data while the triangles are the Validation 1 data. The circles labeled are the Validation 2 data set, and in this example, the Validation 2 data set comprises outlier data points. The plot in FIG. 5 shows qualitatively that the Outlier data points are different from the Calibration and Validation 1 data points.

Figure 6:
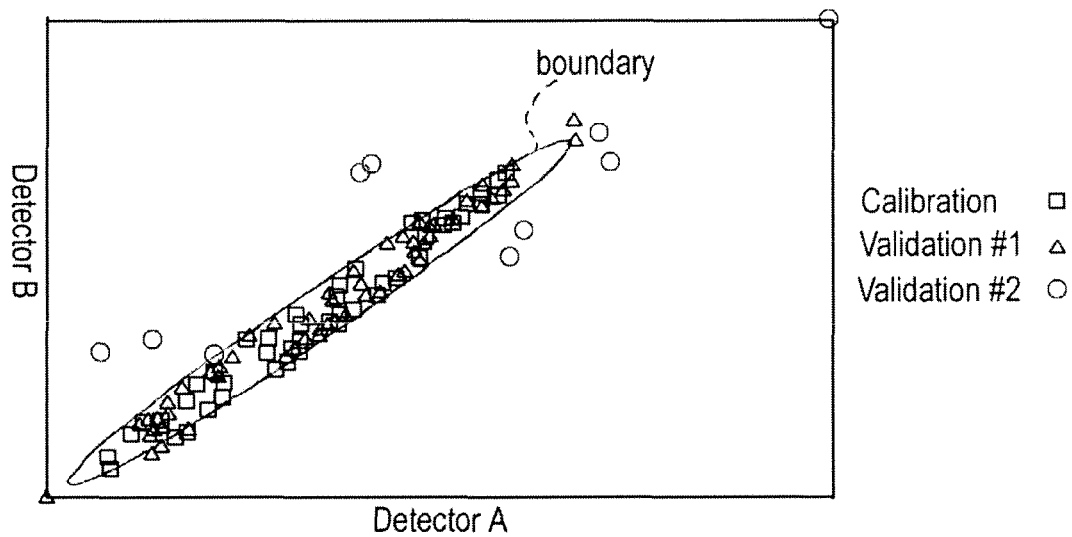
FIG. 6 is a 2-D graph showing data points for the detector outputs of an exemplary optical computing system measuring the same three data sets of FIG. 5.

A similar calculation was made using an optical computing model system and the results are shown in FIG. 6. The optical computing system was designed with a set of spectral elements which frame a particular wavelength region for investigation. In addition, a multivariate optical element (MOE) was designed using the calibration spectra in conjunction with the spectral elements. Specifically, the multivariate optical element was designed based on the data from analyzing the "Calibration" material. The dot product of the transmission of the total optical computing system (including the MOE) with each spectrum was calculated and labeled as Detector A. The dot product of the optical system without the MOE with the sample spectra is Detector B.

FIG. 6 shows a plot of Detector B vs. Detector A for the three different data sets as the example of FIG. 4. Namely, the squares represent the results in the Calibration data set, the triangles represent the Validation 1 data set, and the circles represent the Validation 2 data set. A least squares fit was calculated for the combined Calibration and Validation 1 data set to produce the 2 sigma confidence interval oval labeled as "boundary" in FIG. 6. This oval is a measure of approximately the 95% confidence interval of the data. The same dot products were then calculated for the Validation 2 spectral data and the Detector A and Detector B responses plotted as shown by the circles in FIG. 6. The fact that these circles all fall outside of the 2-sigma oval indicates that these samples are in a different system and the model developed for the Calibration set would not be expected to accurate for this Validation 2 set.

Thus, the present subject matter can be used to determine whether a measurement or sample comes from the expected model universe. For example, an optical analysis system can utilize classification data such as the oval labeled "boundary" in FIG. 6 as a pass/fail determination regarding specific samples. As another example, multiple boundaries can be defined whereby an optical analysis system can determine the 80%, 90%, etc. confidence intervals, which can be used to identify a particular sample as within or outside of the expected universe.

For example, a software application, routine, process, or sub-process may be provided to analyze detector outputs and provide classifying information based on validation data. For instance, the oval labeled as "boundary" in FIG. 6 may be defined as a mathematical function of the signals provided by Detector A and Detector B. When an optical analysis system provides a pair of Detector A and Detector B values, the relative location of the data point as compared to the boundary can be determined and the classifying information can indicate whether the data point is inside, outside, or at the boundary. It will be understood that any appropriate computational method may be used to make the determination and the use of spatial terms (e.g. "inside," "outside," etc.) is for purposes of explanation only.

As another example, validation data may comprise one or more stored records of groupings of data points, such as a first range of data points grouped as "valid," a second range of data points groups as "invalid," and so on. In such embodiments, classification would then be a matter of accessing the record(s) and determining which group a particular data point is associated with. The data points themselves may be stored, or particular ranges may be identified by minimum and maximum values.

As another example, one or more validation/classification circuits may be constructed to provide classification information based on the values of the detector signals. For example, based on the calibration data points, components can be selected so that the output of the circuit(s) vary in a manner consistent with the validation/classification results. For instance components may be selected so that, for detector signal values that correspond to data points in the "valid" range, the classification circuit provides a logical "TRUE" while providing a logical "FALSE" for detector signal values that correspond to data points in the "invalid" range. The TRUE/FALSE indicator (i.e. classification data) can drive an output, such as a green/red LED or any other suitable indicators.

Figure 7:
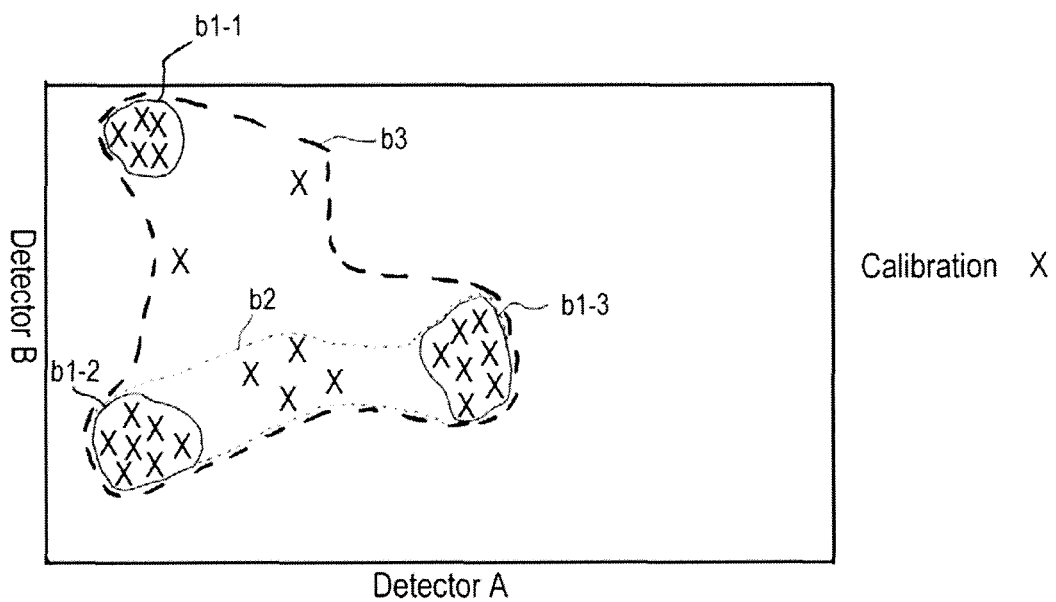
FIG. 7 is a 2-D graph showing hypothetical data points and exemplary corresponding confidence intervals that may be used to classify measurement data.

FIG. 7 is another 2-D graph of calibration data points. In this example, hypothetical calibration data points are illustrated as a plurality of "X"s in the graph. Furthermore, in this example, the hypothetical data points appear in several dispersed clusters. Five boundaries are defined in this example: boundaries b1-1, b1-2, and b1-3 each define a cluster; boundary b2 defines an area comprising the clusters b1-1 and b1-3 and some additional data points, while boundary b3 defines an area including all hypothetical data points.

The various boundaries b1, b2, and b3 may be used to define validation data that comprises multiple confidence levels. For instance, data points within either of boundaries b1-1, b1-2, or b1-3 may be deemed to lie in a "high" confidence level due to the clusters in those areas. Data points within boundary b2 may be deemed to lie in a "medium" confidence level since the calibration data indicates a possibility of data points in the area, but not as high a possibility as compared to the clusters. Data points within boundary b3 may be deemed to lie in a "low" confidence area, since it is possible for data points to be valid in the area but not likely. Data points outside boundary b3 may be deemed to lie in a "no" confidence area since, in this example, no calibration data points occur outside boundary b3. It will be understood, of course, that these exemplary data points and boundaries are hypothetical in nature and are not intended to represent any real materials or test results.

Data defining boundaries b1, b2, and b3 may be provided for use in evaluating optical analysis system measurements. For example, as noted above, software (and/or hardware) may evaluate a measurement data point based on the validation data to determine a confidence level of a measurement derived from the data point. In this example, since multiple boundaries are defined, the classification process can include more sophisticated logic. For example, a routine may first determine if a data point lies within boundary b3; if so, the data point may be evaluated to determine which (if any) further boundary the point lies within, and so on. Similarly, if an evaluation circuit or circuits are constructed, then the circuit can be designed so that the range of possible outputs of the circuit varies according to the confidence level.

Output for the different confidence levels may be provided in any suitable manner. For example, if the boundaries define different percentage levels of confidence, the confidence level can be output to a display alongside measurement results. Alternatively or additionally, an indicator, such as a colored light associated with each level (e.g. green for "high confidence", yellow for "medium confidence", red for "low confidence," and blinking red for "no confidence").

Although the above examples discussed discrete confidence levels, in other embodiments, confidence levels could be evaluated across a continuous spectrum by an appropriate mathematical model constructed from calibration data.

Figure 8:
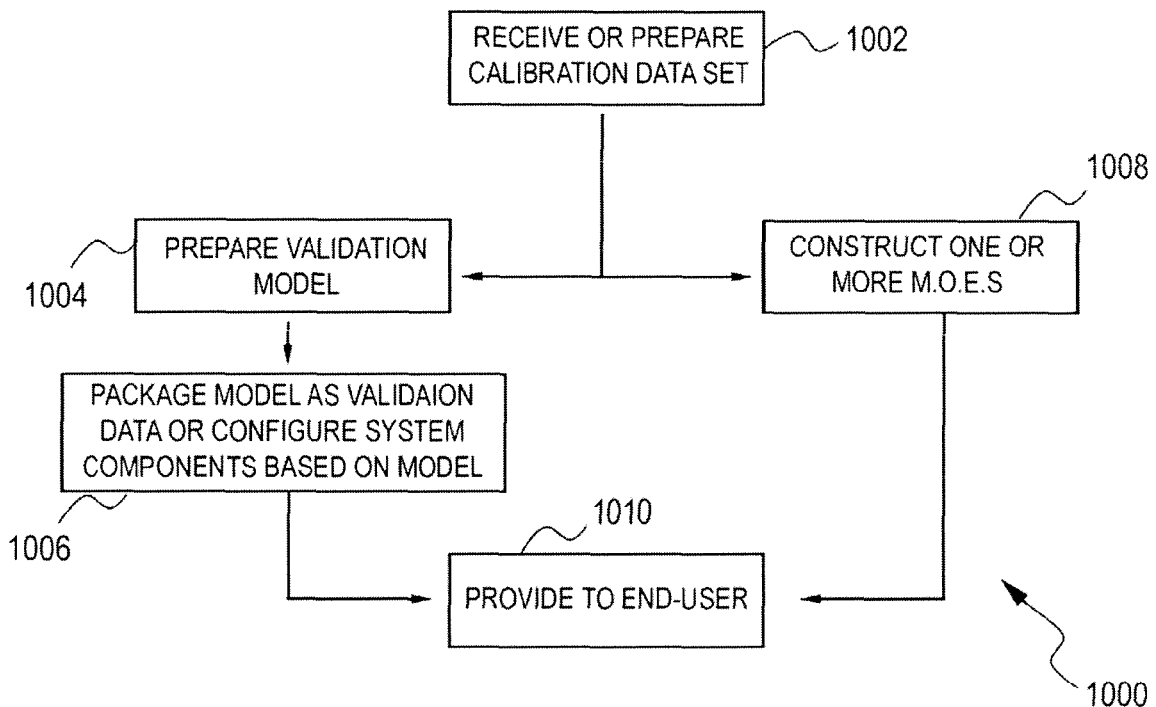
FIG. 8 is a process flow showing exemplary steps that may be carried out to provide measurement classification capability.

A manufacturer or other entity building or configuring an optical analysis system can obtain calibration data to construct one or more multivariate optical elements for use in the system. The same calibration data can be used to construct one or more validation models. This is shown in exemplary process 1000 of FIG. 8. At 1002, a calibration data set is received or prepared. For example, a manufacturer may receive test results from a plurality of samples having known properties. At 1008, one or more multivariate optical elements (MOEs) are constructed or configured based on the calibration data set. Based on the same calibration data set, at 1004 a validation model or models are prepared. Calibration data can be evaluated in any suitable way in order to prepare validation data for use in classifying optical analysis system measurements. For instance, as noted above, one or more equations or models may be developed based on calibration data, and/or listings of data points and associated classifications may be prepared based in whole or in part on test results. The particulars of the model(s) will depend on the needs of the end user, such as desired granularity and type of classification. For instance, some users may want a binary "valid" or "invalid" indication while others may desire a percentage indicator of confidence.

At 1006, the model(s) are packaged into suitable validation data or system components are configured according to the model. For example, the models may be converted into one or more files stored in computer-readable media if a digital computer is used to classify/validate results. The particular format and data structures that are used can vary, of course. If one or more analog circuits are used to classify/validate results, then circuit components (e.g. resisters, capacitors, inductors, transistors, logic components, etc.) are selected and arranged to provide classification data in accordance with the model.

At 1010, both the multivariate optical element and validation data (or evaluation circuit(s)) are provided to the end user. For instance, one or more validation files may be provided for a particular multivariate optical element. The models can be provided to an end-user of the optical analysis system as validation data for use in the validation/classification process. In some cases, if the same multivariate optical element is used to analyze multiple different materials, additional validation files or circuits with appropriate responses for the additional material(s) can be provided.

Figure 9:
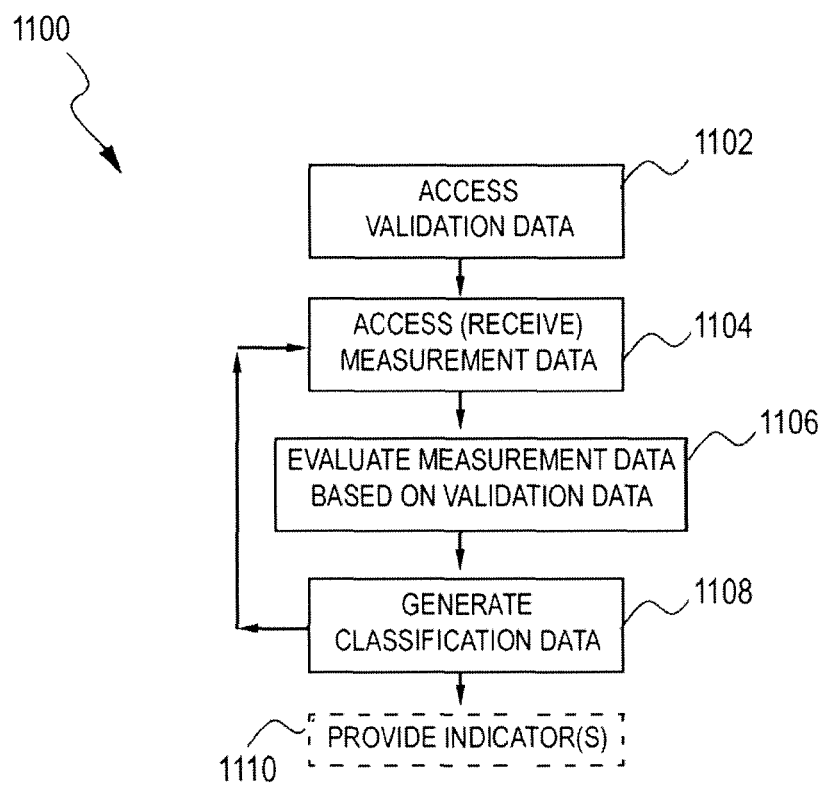
FIG. 9 is a process flow showing exemplary steps in a classification routine.

FIG. 9 illustrates an exemplary process 1100 that may be carried out to classify signals obtained using an optical analysis system. For example, process 1100 may represent a software routine, process, or component whereby one or more measurements may be classified based on the values of light signals that are used to obtain the measurements. Of course, some or all aspects of the process could be implemented using specialized hardware, in which case validation data would not be accessed inasmuch as the data would be embodied in the circuitry used to evaluate measurement signals. In other embodiments, a combination of hardware- and software-based classification/evaluation may be used, of course.

The validation process may be carried out alone or alongside or as part of one or more other processes, such as chemometric or other analysis of data. For instance, in some embodiments, one or more classification processes using data from an optical analysis system are carried out in parallel, shortly after, or shortly before one or more other processes that provide a substantive measurement based on the data.

At 1102, validation data is accessed. For example, one or more data files comprising validation data for use with a particular multivariate optical element may be accessed. At 1104, measurement data is accessed or received. For example, signals from sensors, such as Signal A and Signal B, may be received from an optical analysis system, with classification occurring in real time or near real-time as the data is received. As another example, stored data representing Signal A and Signal B may be accessed for off-line classification and/or analysis. At 1106, the measurement data is evaluated based on the validation data, and at 1108 classification data is generated. The evaluation process and resulting classification will depend on factors such as the type of validation model as well as the types and degree of granularity provided for classification.

At step 1110, one or more indicators are provided to indicate the classification results. For example, as was noted above, classification may be indicated using color-coded lights or data outputs, such as confidence percentages. The type of indication, if any, may depend on the classification results in some embodiments. Additionally, end-users and/or the system manufacturer may specify the type of indicators and the conditions that trigger the indicators. Any suitable indicator or indicators may be used however, including, but not limited to, visual effects (e.g. colors, flashing lights, icons), sound effects (such as computer sound effects, alarm klaxons), and the like. Indicators may also comprise data that is sent to other systems, such as other computer or control systems in a facility. In some embodiments, indicators may not always be provided at the time data is classified, and so step 1110 is illustrated using dashed lines. For instance, measurements may be classified and the classification data stored for later analysis.

This embodiment of process 1100 is shown to loop back to 1104 from 1108 in order to represent ongoing classification of data. However, it will be understood that looping need not necessarily occur; for instance, if no more measurement data remains (i.e. a particular measurement cycle is complete or a stored set of data has been classified), then the process can end.

The previously-mentioned U.S. Provisional Patent Application Ser. No. 60/816,416, filed Jun. 26, 2006, is hereby incorporated by reference herein in its entirety It is appreciated by persons skilled in the art that what has been particularly shown and described above is not meant to be limiting, but instead serves to show and teach various exemplary implementations of the present subject matter. As set forth in the attached claims, the scope of the present invention includes both combinations and sub-combinations of various features discussed herein, along with such variations and modifications as would occur to a person of skill in the art.

What is claimed:

1. A method of classifying measurement results in a multivariate optical computing system, the method comprising:
  receiving a first signal based on a first portion of an illumination light that has interacted with a sample, the first signal modified by at least one spectral element;
  receiving a second signal based on the first portion of the illumination light;
  separating a second portion of the illumination light from a first portion of the illumination light before the first portion of the illumination light has interacted with the sample;
  determining a baseline for the first signal and the second signal using a calibration signal from the second portion of the illumination light, the calibration signal modified by the at least one spectral element; and
  providing classifying information based on determining if the first signal and the second signal lie in a range of expected results.

2. The method as set forth in claim 1, wherein the at least one spectral element comprises a multivariate optical element.

3. The method as set forth in claim 2, wherein the first signal represents the dot product of a spectrum of light with a weighted regression vector.

4. The method as set forth in claim 1, wherein providing classifying information is further based on validation data indicating a range of expected results.

5. A method of classifying measurement results in a multivariate optical computing system, the method comprising:
receiving a first signal based on light that has interacted with a material of interest and at least one spectral element;
receiving a second signal based on light that has interacted with the material of interest; and
providing classifying information based on determining if the first signal and the second signal lie in a range of expected results;
wherein the validation data comprises data indicating at least one boundary that defines expected results as a function of the value of the first and second signal; and
wherein providing classifying information comprises determining where a given pair of simultaneous values for the first and second signal lie relative to the at least one boundary.

6. The method as set forth in claim 1, wherein providing classifying information comprises indicating whether a measurement is valid.

7. The method as set forth in claim 1, wherein providing classifying information comprises indicating a confidence interval in which a measurement lies.

8. The method as set forth in claim 1, further comprising providing at least one measurement result based on data including the first and second signals and providing at least one indicator alongside or as part of the at least one measurement.

9. An optical computing system comprising at least one computing device, the at least one computing device adapted to:
receive data from a first detector indicative of a first portion of an illumination light that has interacted with a sample, the first signal modified by at least one spectral element;
receive data from a second detector indicative of the first portion of the illumination light;
separating a second portion of the illumination light from a first portion of the illumination light before the first portion of the illumination light has interacted with the sample;
determining a baseline for the data from the first and second detectors using a calibration signal from the second portion of the illumination light, the calibration signal modified by the at least one spectral element; and
produce classification data based on determining if the data from the first and second detectors lie in a range of expected results.

10. The system as set forth in claim 9, wherein the at least one computing device is further adapted to access validation data and to produce classification data based on evaluating the data from the first and second detectors and the validation data.

11. An optical computing system comprising at least one computing device, the at least one computing device adapted to:
receive data from a first detector indicative of light that has interacted with a material of interest and at least one spectral element;
receive data from a second detector indicative of light that has interacted with the material of interest; and
produce classification data based on determining if the data from the first and second detectors lie in a range of expected results;
wherein the at least one computing device is further adapted to access validation data and to produce classification data based on evaluating the data from the first and second detectors and the validation data;
wherein the validation data comprises data indicating at least one boundary that defines expected results as a function of the value of the first and second signal; and
wherein producing classification data comprises determining where a given pair of simultaneous values for the first and second signal lie relative to the at least one boundary.

12. The system as set forth in claim 9, wherein the classification data comprises an indicator of whether a measurement based on data from at least one of the first and second detectors is valid.

13. The system as set forth in claim 9, wherein the classification data comprises an indicator of a confidence interval of a measurement based on data from at least one of the first and second detectors.

14. The system as set forth in claim 9, wherein the at least one computing device is further adapted to:
provide at least one measurement result based on data from the first and second detectors; and
provide at least one indicator of the classification data alongside or as part of the at least one measurement result.

15. The system as set forth in claim 9, further comprising:
at least one light source configured to illuminate a material of interest;
first and second broadband detectors each configured to detect light over a wavelength range and to provide data to the at least one computing device; and
a multivariate optical element positioned to interact with light from the material of interest;
wherein said first broadband detector is positioned to receive light that has interacted with the material of interest and the multivariate optical element; and
wherein said second broadband detector is positioned to receive light that has interacted with the material of interest, but not the multivariate optical element.

16. The system as set forth in claim 9, wherein the at least one computing device comprises a computer adapted by software to receive data and produce classification data.

17. A method of configuring a measurement system, the method comprising:
obtaining calibration data, the calibration data comprising a plurality of data points;
based on the calibration data, constructing at least one multivariate optical element based on the data points;
based on the data points, preparing a validation model, the validation model comprising a boundary of values dividing an area into a valid result area and an invalid result area;
including the at least one multivariate optical element in a measurement system comprising at least one controller; and
configuring the at least one controller to validate measurement results based on the validation model.

18. The method of claim 17, wherein validation model further comprises a two-dimensional area defined by the plurality of data points, the two-dimensional area comprising one or more boundaries.

19. The method of claim 1 wherein the sample comprises oil contained in water or water contained in oil.

20. A method of classifying measurement results in a multivariate optical computing system, the method comprising:
- receiving a first signal based on a first portion of an illumination light that has interacted with a material of interest, the first signal modified by at least one spectral element;
- receiving a second signal based on the first portion of the illumination light;
- providing classifying information based on determining if the first signal and the second signal lie in a range of expected results; and
- determining a baseline of at least one of the first signal and the second signal using a second portion of the illumination light, wherein:
- the second portion of the illumination light is separated from the first portion of the illumination light before the first portion of the illumination light has interacted with the sample.

21. An optical computing system comprising at least one computing device, the at least one computing device adapted to:
- receive data from a first detector indicative of a first portion of an illumination light that has interacted with a sample, the first signal modified by at least one spectral element;
- receive data from a second detector indicative of the first portion of the illumination light;
- determine a baseline for at least one of the data from a first detector and the second detector using data indicative of a second portion of the illumination light, wherein:
- the second portion of the illumination light is separated from the first portion of the illumination light before the first portion of the illumination light has interacted with the sample; and
- produce classification data based on determining if the data from the first and second detectors lie in a range of expected results.

22. The method of claim 5 wherein the material of interest comprises oil contained in water or water contained in oil.

23. The method of claim 5 wherein the classifying information comprises an octane rating or a lead content in a gasoline sample.

24. The optical computing system of claim 11 wherein the material of interest comprises oil contained in water or water contained in oil.

25. The optical computing system of claim 11 wherein the classifying information comprises an octane rating or a lead content in a gasoline sample.

26. The method of claim 20 wherein the sample comprises oil contained in water or water contained in oil.

27. The method of claim 20 wherein the classifying information comprises an octane rating or a lead content in a gasoline sample.

28. The optical computing system of claim 21 wherein the material of interest comprises oil contained in water or water contained in oil.

29. The optical computing system of claim 21 wherein the classifying information comprises an octane rating or a lead content in a gasoline sample.

* * * * *